(12) United States Patent (10) Patent No.: US 7,442,556 B2
Manger et al. (45) Date of Patent: Oct. 28, 2008

(54) MICROFLUIDIC-BASED ELECTROSPRAY SOURCE FOR ANALYTICAL DEVICES WITH A ROTARY FLUID FLOW CHANNEL FOR SAMPLE PREPARATION

(75) Inventors: Ian David Manger, Palo Alto, CA (US); Cunsheng Casey Hao, Cupertino, CA (US); Marc Alexander Unger, South San Francisco, CA (US)

(73) Assignee: Fluidigm Corporation, South San Francisco, CA (US)

( * ) Notice: Subject to any disclaimer, the term of this patent is extended or adjusted under 35 U.S.C. 154(b) by 81 days.

(21) Appl. No.: 11/302,605

(22) Filed: Dec. 13, 2005

(65) Prior Publication Data

US 2006/0099116 A1    May 11, 2006

Related U.S. Application Data

(63) Continuation of application No. 09/687,401, filed on Oct. 13, 2000, now abandoned.

(51) Int. Cl.
*G01N 1/10* (2006.01)
*B01D 59/44* (2006.01)

(52) U.S. Cl. .................. 436/180; 250/281; 250/282; 250/288; 422/58; 422/70; 422/81; 422/100; 436/52; 436/161; 436/173; 436/174; 436/175; 436/177; 436/183

(58) Field of Classification Search .......... 250/281–282, 250/288; 422/58–59, 68.1–70, 81, 100; 435/6; 436/52, 86–87, 89, 91, 93–94, 161, 173–175, 436/177, 183, 518, 526, 530, 180
See application file for complete search history.

(56) References Cited

U.S. PATENT DOCUMENTS

| 2,656,508 | A | 10/1953 | Coulter |
| 3,570,515 | A | 3/1971 | Kinner |
| 3,747,628 | A | 7/1973 | Holster et al. |
| 3,839,176 | A | 10/1974 | McCoy et al. |
| 3,915,652 | A | 10/1975 | Natelson |
| 3,984,307 | A | 10/1976 | Kamentsky et al. |
| 4,046,159 | A | 9/1977 | Pegourie |

(Continued)

FOREIGN PATENT DOCUMENTS

EP    0 592 094 A2    4/1994

(Continued)

OTHER PUBLICATIONS

"Biochips," Nature Biotechnology, vol. 18, Supplement 2000, pp. IT43-IT44, 2000.

(Continued)

*Primary Examiner*—Arien Soderquist
(74) *Attorney, Agent, or Firm*—Townsend and Townsend and Crew LLP

(57) ABSTRACT

This invention provides microfluidic devices and methods for using the same. Microfluidic devices of the present invention comprises a first elastic layer, a fluid flow channel within the elastic layer; and a means for providing a fluid sample from the fluid flow channel to an analytical device. The present invention also provides an analytical apparatus comprising such a microfluidic device and an analytical device.

25 Claims, 9 Drawing Sheets

U.S. PATENT DOCUMENTS

| | | |
|---|---|---|
| 4,119,368 A | 10/1978 | Yamakazi |
| 4,153,855 A | 5/1979 | Feingold |
| 4,245,673 A | 1/1981 | Bouteille et al. |
| 4,373,527 A | 2/1983 | Fischell |
| 4,399,219 A | 8/1983 | Weaver |
| 4,434,704 A | 3/1984 | Surjaatmadja |
| 4,575,681 A | 3/1986 | Grosso et al. |
| 4,581,624 A | 4/1986 | O'Connor |
| 4,585,209 A | 4/1986 | Aine et al. |
| 4,662,710 A | 5/1987 | ten Berge |
| 4,675,300 A | 6/1987 | Zare et al. |
| 4,786,165 A | 11/1988 | Yamamoto et al. |
| 4,797,842 A | 1/1989 | Nackman et al. |
| 4,876,504 A | 10/1989 | Blake et al. |
| 4,898,582 A | 2/1990 | Faste |
| 4,908,112 A | 3/1990 | Pace |
| 4,936,465 A | 6/1990 | Zold |
| 4,963,498 A | 10/1990 | Hillman et al. |
| 4,965,743 A | 10/1990 | Malin et al. |
| 4,992,312 A | 2/1991 | Frisch |
| 5,032,381 A | 7/1991 | Bronstein et al. |
| 5,085,562 A | 2/1992 | Van Lintel |
| 5,088,515 A | 2/1992 | Kamen |
| 5,096,388 A | 3/1992 | Weinberg |
| 5,100,627 A | 3/1992 | Buican et al. |
| 5,126,022 A | 6/1992 | Soane et al. |
| 5,126,115 A | 6/1992 | Fujita et al. |
| 5,164,558 A | 11/1992 | Huff et al. |
| 5,171,132 A | 12/1992 | Miyazaki |
| 5,171,764 A | 12/1992 | Katayama et al. |
| 5,224,843 A | 7/1993 | Van Lintel |
| 5,259,737 A | 11/1993 | Kamisuki et al. |
| 5,265,327 A | 11/1993 | Faris et al. |
| 5,290,240 A | 3/1994 | Horres, Jr. |
| 5,307,186 A | 4/1994 | Izumi et al. |
| 5,336,062 A | 8/1994 | Richter |
| 5,346,372 A | 9/1994 | Naruse et al. |
| 5,375,979 A | 12/1994 | Trah |
| 5,376,252 A | 12/1994 | Ekstrom |
| 5,400,741 A | 3/1995 | DeTitta et al. |
| 5,423,287 A | 6/1995 | Usami et al. |
| 5,434,047 A | 7/1995 | Arnold et al. |
| 5,452,878 A | 9/1995 | Gravesen et al. |
| 5,454,472 A | 10/1995 | Benecke et al. |
| 5,487,003 A | 1/1996 | Iwasawa et al. |
| 5,496,009 A | 3/1996 | Farrell et al. |
| 5,498,392 A | 3/1996 | Wilding et al. |
| 5,500,071 A | 3/1996 | Kaltenbach et al. |
| 5,512,131 A | 4/1996 | Kumar et al. |
| 5,525,464 A | 6/1996 | Drmanac et al. |
| 5,529,465 A | 6/1996 | Zengerle et al. |
| 5,558,998 A | 9/1996 | Hammond et al. |
| 5,571,410 A | 11/1996 | Swedberg et al. |
| 5,574,893 A | 11/1996 | Southgate et al. |
| 5,580,523 A | 12/1996 | Bard |
| 5,587,128 A | 12/1996 | Wilding et al. |
| 5,589,136 A | 12/1996 | Northrup et al. |
| 5,593,130 A | 1/1997 | Hansson et al. |
| 5,595,650 A | 1/1997 | Manz |
| 5,608,519 A | 3/1997 | Gourley |
| 5,632,876 A | 5/1997 | Zanzucchi et al. |
| 5,641,400 A | 6/1997 | Kaltenbach et al. |
| 5,642,015 A | 6/1997 | Whitehead et al. |
| 5,656,155 A | 8/1997 | Norcross et al. |
| 5,659,171 A | 8/1997 | Young et al. |
| 5,660,370 A | 8/1997 | Webster |
| 5,661,222 A | 8/1997 | Hare |
| 5,665,070 A | 9/1997 | McPhee |
| 5,681,024 A | 10/1997 | Lisec et al. |
| 5,702,618 A | 12/1997 | Saaski et al. |
| 5,705,018 A | 1/1998 | Hartley |
| 5,716,852 A | 2/1998 | Yager et al. |
| 5,726,751 A | 3/1998 | Altendorf et al. |
| 5,750,015 A | 5/1998 | Soane et al. |
| 5,757,482 A | 5/1998 | Fuchs et al. |
| 5,759,014 A | 6/1998 | Van Lintel |
| 5,775,371 A | 7/1998 | Pan et al. |
| 5,779,868 A | 7/1998 | Parce et al. |
| 5,788,468 A | 8/1998 | Dewa et al. |
| 5,800,690 A | 9/1998 | Chow et al. |
| 5,807,522 A | 9/1998 | Brown et al. |
| 5,812,394 A | 9/1998 | Lewis et al. |
| 5,833,926 A | 11/1998 | Wurzel et al. |
| 5,836,750 A | 11/1998 | Cabuz |
| 5,837,200 A | 11/1998 | Diessel et al. |
| 5,839,722 A | 11/1998 | Berlin et al. |
| 5,842,787 A | 12/1998 | Kopf-Sill et al. |
| 5,852,495 A | 12/1998 | Parce |
| 5,854,684 A | 12/1998 | Stabile et al. |
| 5,856,174 A | 1/1999 | Lipshutz et al. |
| 5,858,187 A | 1/1999 | Ramsey et al. |
| 5,858,649 A | 1/1999 | Asgari et al. |
| 5,863,502 A | 1/1999 | Southgate et al. |
| 5,863,801 A | 1/1999 | Southgate et al. |
| 5,867,399 A | 2/1999 | Rostoker et al. |
| 5,869,004 A | 2/1999 | Parce et al. |
| 5,872,010 A | 2/1999 | Karger et al. |
| 5,875,817 A | 3/1999 | Carter |
| 5,876,187 A | 3/1999 | Afromowitz |
| 5,880,071 A | 3/1999 | Parce et al. |
| 5,885,470 A | 3/1999 | Parce et al. |
| 5,904,824 A | 5/1999 | Oh |
| 5,932,799 A | 8/1999 | Moles |
| 5,942,443 A | 8/1999 | Parce et al. |
| RE36,350 E | 10/1999 | Swedberg et al. |
| 5,971,355 A | 10/1999 | Biegelsen et al. |
| 5,994,696 A | 11/1999 | Tai et al. |
| 5,997,961 A | 12/1999 | Feng et al. |
| 6,004,442 A | 12/1999 | Choulga et al. |
| 6,007,309 A | 12/1999 | Hartley |
| 6,042,709 A | 3/2000 | Parce et al. |
| 6,043,080 A | 3/2000 | Lipshutz et al. |
| 6,048,498 A | 4/2000 | Kennedy |
| 6,056,428 A | 5/2000 | Devoino et al. |
| 6,089,534 A | 7/2000 | Biegelsen et al. |
| 6,103,537 A | 8/2000 | Ullman et al. |
| 6,107,044 A | 8/2000 | Nikiforov |
| 6,123,769 A | 9/2000 | Sanjoh |
| 6,132,685 A | 10/2000 | Kercso et al. |
| 6,149,787 A | 11/2000 | Chow et al. |
| 6,149,870 A | 11/2000 | Parce et al. |
| 6,155,282 A | 12/2000 | Zachary et al. |
| 6,167,910 B1 | 1/2001 | Chow |
| 6,174,365 B1 | 1/2001 | Sanjoh |
| 6,182,020 B1 | 1/2001 | Fairbanks |
| 6,221,654 B1 | 4/2001 | Quake et al. |
| 6,235,175 B1 | 5/2001 | Dubrow et al. |
| 6,246,330 B1 | 6/2001 | Nielsen |
| 6,274,337 B1 | 8/2001 | Parce et al. |
| 6,296,673 B1 | 10/2001 | Santarsiero et al. |
| 6,321,791 B1 | 11/2001 | Chow |
| 6,329,209 B1 | 12/2001 | Wagner et al. |
| 6,345,502 B1 | 2/2002 | Tai et al. |
| 6,358,387 B1 | 3/2002 | Kopf-Sill et al. |
| 6,375,871 B1 | 4/2002 | Bentsen et al. |
| 6,376,971 B1 | 4/2002 | Petrine et al. |
| 6,408,878 B2 | 6/2002 | Unger et al. |
| 6,409,832 B2 | 6/2002 | Weigl et al. |
| 6,488,832 B2 | 12/2002 | Heller |
| 6,488,872 B1 | 12/2002 | Beebe et al. |
| 6,500,323 B1 | 12/2002 | Chow et al. |
| 6,508,988 B1 | 1/2003 | Van Dam et al. |
| 6,520,936 B1 | 2/2003 | Mann |
| 6,533,914 B1 | 3/2003 | Liu |

| | | |
|---|---|---|
| 6,537,799 B2 | 3/2003 | Chow et al. |
| 6,540,895 B1 | 4/2003 | Quake et al. |
| 6,541,071 B1 | 4/2003 | Bookbinder et al. |
| 6,563,111 B1 | 5/2003 | Moon et al. |
| 6,569,382 B1 | 5/2003 | Edman et al. |
| 6,581,441 B1 | 6/2003 | Paul |
| 6,585,939 B1 | 7/2003 | Dapprich |
| 6,596,545 B1 | 7/2003 | Wagner et al. |
| 6,605,472 B1 | 8/2003 | Skinner et al. |
| 6,637,463 B1 | 10/2003 | Lei et al. |
| 6,662,818 B2 | 12/2003 | Paul et al. |
| 6,664,104 B2 | 12/2003 | Pourahmadi et al. |
| 6,667,124 B2 | 12/2003 | Suenaga et al. |
| 6,677,131 B2 | 1/2004 | Yuen |
| 6,713,327 B2 | 3/2004 | Leedy |
| 6,716,378 B2 | 4/2004 | Yang et al. |
| 6,736,978 B1 | 5/2004 | Porter et al. |
| 6,749,814 B1 | 6/2004 | Bergh et al. |
| 6,752,922 B2 | 6/2004 | Huang et al. |
| 6,765,279 B2 | 7/2004 | Leedy |
| 6,767,706 B2 | 7/2004 | Quake et al. |
| 6,829,753 B2 | 12/2004 | Lee et al. |
| 6,960,437 B2 | 11/2005 | Enzelberger et al. |
| 2001/0027745 A1 | 10/2001 | Weigl et al. |
| 2001/0041357 A1 | 11/2001 | Fouillet et al. |
| 2002/0005354 A1 | 1/2002 | Spence et al. |
| 2002/0014673 A1 | 2/2002 | Leedy |
| 2002/0037499 A1 | 3/2002 | Quake et al. |
| 2002/0045297 A1 | 4/2002 | Leedy |
| 2002/0058332 A1 | 5/2002 | Quake et al. |
| 2002/0064885 A1 | 5/2002 | Bedingham et al. |
| 2002/0108096 A1 | 8/2002 | Lee et al. |
| 2002/0108097 A1 | 8/2002 | Harris et al. |
| 2002/0109114 A1 | 8/2002 | Driggs et al. |
| 2002/0127736 A1 | 9/2002 | Fu et al. |
| 2002/0145231 A1 | 10/2002 | Hansen et al. |
| 2002/0158022 A1 | 10/2002 | Huang et al. |
| 2002/0197603 A1 | 12/2002 | Chow et al. |
| 2003/0008308 A1 | 1/2003 | Enzelberger et al. |
| 2003/0049659 A1 | 3/2003 | Lapidus et al. |
| 2003/0143120 A1 | 7/2003 | Ruediger et al. |
| 2003/0175947 A1 | 9/2003 | Liu et al. |
| 2004/0072278 A1 | 4/2004 | Chou et al. |
| 2004/0096960 A1 | 5/2004 | Mehta et al. |
| 2004/0141887 A1 | 7/2004 | Mainquist et al. |
| 2004/0209354 A1 | 10/2004 | Mathies et al. |
| 2004/0248167 A1 | 12/2004 | Quake et al. |
| 2005/0000900 A1 | 1/2005 | Huang et al. |
| 2005/0019792 A1 | 1/2005 | McBride et al. |
| 2005/0053952 A1 | 3/2005 | Hong et al. |
| 2005/0065735 A1 | 3/2005 | Lee et al. |
| 2005/0164376 A1 | 7/2005 | Balagadde et al. |
| 2005/0180891 A1 | 8/2005 | Webster |

FOREIGN PATENT DOCUMENTS

| | | |
|---|---|---|
| EP | 0 706 004 A2 | 4/1996 |
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| EP | 1 065 378 A2 | 1/2001 |
| GB | 2 097 692 A | 11/1982 |
| GB | 2 155 152 A | 9/1985 |
| GB | 2 308 460 A | 6/1997 |
| WO | WO 98/07069 A1 | 2/1998 |
| WO | WO 98/39645 A1 | 9/1998 |
| WO | WO 98/52691 A1 | 11/1998 |
| WO | WO 99/00655 A2 | 1/1999 |
| WO | WO 99/04361 A1 | 1/1999 |
| WO | WO 99/17093 A1 | 4/1999 |
| WO | WO 99/52633 A1 | 10/1999 |
| WO | WO 99/61888 A2 | 12/1999 |
| WO | WO 00/00678 A1 | 1/2000 |
| WO | WO 00/21666 A1 | 4/2000 |
| WO | WO 00/22409 A2 | 4/2000 |
| WO | WO 00/30167 A1 | 5/2000 |
| WO | WO 00/43748 A1 | 7/2000 |
| WO | WO 00/60345 A1 | 10/2000 |
| WO | WO 01/01025 A2 | 1/2001 |
| WO | WO 01/06575 A1 | 1/2001 |
| WO | WO 01/09595 A2 | 2/2001 |
| WO | WO 01/09595 A3 | 2/2001 |
| WO | WO 01/53794 A1 | 7/2001 |
| WO | WO 01/94635 A2 | 12/2001 |
| WO | WO 02/30486 A2 | 4/2002 |
| WO | WO 02/43615 A2 | 6/2002 |
| WO | WO 02/60582 A3 | 8/2002 |
| WO | WO 03/037781 A1 | 5/2003 |

OTHER PUBLICATIONS

"Chapter 9: Microfluidic Devices," Micromachined Transducers Sourcebook, pp. 779-882, 1998.

Ahn, Chong H. et al., "Fluid Micropumps Based On Rotary Magnetic Actuators," Proceedings of 1995 IEEE Micro Electro Mechanical Systems Workshop (MEMS) '95), Amsterdam, Netherlands, pp. 408-412, Jan. 29-Feb. 2, 1995.

Anderson, Janelle R. et al., "Fabrication Of Topologically Complex Three-Dimensional Microfluidic Systems In PDMS By Rapid Prototyping," Analytical Chemistry, vol. 72, No. 14, pp. 3158-3164, Jul. 15, 2000.

Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

Angell, James B. et al., "Silicon Micromechanical Devices," Scientific American, pp. cover, 44-55, Apr. 1983.

Armani, Deniz et al., "Re-Configurable Fluid Circuits By PDMS Elastomer Micromachining," IEEE Int. Conf. Micro Electro Mech. Syst. Tech. Digest, vol. 12, pp. 222-227, 1999.

Ballantyne, J. P. et al., "Selective Area Metallization By Electron-Beam Controlled Direct Metallic Deposition," J. Vac. Sci. Technol., vol. 10, No. 6, pp. 1094-1097, Nov. 1973.

Benard, W. L. et al., "A Titanium-Nickel Shape-Memory Alloy Actuated Micropump," Transducers '97, 1997 International Conference on Solid-State Sensors and Actuators, Chicago, Illinois, pp. 361-364, Jun. 16-19, 1997.

Bloomstein, T. M. et al., "Laser-Chemical Three-Dimensional Writing For Microelectromechanics And Application To Standard-Cell Microfluidics," J. Vac. Sci. Technol. B, vol. 10, No. 6, pp. 2671-2674, Nov. 1992.

Bousse, Luc et al., "Electrokinetically Controlled Microfluidic Analysis Systems," Annu. Rev. Biophys. Biomol. Struct., vol. 29, pp. 155-181, 2000.

Brechtel, R. et al., "Control Of The Electroosmotic Flow By Metal-Salt-Containing Buffers," Journal of Chromatograpy A, vol. 716, pp. 97-105, 1995.

Bryzek, Janusz et al., "Micromachines On The March", IEEE Spectrum, vol. 31, No. 5, pp. 20-31, May 1994.

Buchaillot, Lionel et al., "Silicon Nitride Thin Films Young's Modulus Determination By An Optical Non Destructive Method," Jpn. J. Appl. Phys., vol. 36, Part. 2, No. 6B, pp. L794-L797, Jun. 15, 1997.

Chan, Jason H. et al., "Microfabricated Polymer Devices For Automated Sample Delivery Of Peptides For Analysis By Electrospray Ionization Tandem Mass Spectrometry," Analytical Chemistry, vol. 71, No. 20, pp. 4437-4444, Oct. 15, 1999.

Chiang, Yuh-Min et al. "Characterizing The Process Of Cast Molding Microfluidic Systems," SPIE, vol. 3877, pp. 303-311, Sep. 1999.

Chiu, Daniel T. et al., "Patterned Deposition Of Cells And Proteins Onto Surfaces By Using Three-Dimensional Microfluidic Systems," PNAS, vol. 97, No. 6, pp. 2408-2413, Mar. 14, 2000.

Chou, Hou-Pu et al., "A Microfabricated Device For Sizing and Sorting DNA Molecules," Proc. Natl. Acad. Sci., vol. 96, pp. 11-13, Jan. 1999.

Chou, Hou-Pu et al., "Integrated Elastomer Fluidic Lab-On-A-Chip-Surface Patterning And DNA Diagnostics," Proceedings of the Solid State Actuator and Sensor Workshop, Hilton Head, South Carolina, 4 pages, 2000.

Chou, Hou-Pu et al., "Multiple Disease Diagnostics On A Single Chip," Biophysics Lab, Caltech, pp. 1-4, Mar. 1, 2000.

Delamarche, Emmanuel et al., "Patterned Delivery Of Immunoglobulins To Surfaces Using Microfluidic Networks," Science, vol. 276, pp. 779-781, May 2, 1997.

Dharmatilleke, Saman et al., "Three-Dimensional Silicone Device Fabrication and Interconnection Scheme For Microfluidic Applications Using Sacrificial Wax Layers," Micro-Electro-Mechanical Systems (MEMS), vol. 2, pp. 413-418, 2000.

Duffy, David C. et al., "Patterning Electroluminescent Materials With Feature Sizes As Small As 5μm Using Elastomeric Membranes As Masks For Dry Lift-Off," Advanced Materials, vol. 11, No. 7, pp. 546-552, 1999.

Duffy, David C. et al., "Rapid Prototyping Of Microfluidic Switches In Poly(dimethyl siloxane) And Their Actuation By Electro-Osmotic Flow," J. Micromech. Microeng., vol. 9, pp. 211-217, 1999.

Duffy, David C. et al., "Rapid Prototyping Of Microfluidic Systems In Poly(dimethylsiloxane)," Analytical Chemistry, vol. 70, No. 23, pp. 4974-4984, Dec. 1, 1998.

Effenhauser, Carlo S. et al., "Integrated Capillary Electrophoresis On Flexible Silicone Microdevices: Analysis Of DNA Restriction Fragments And Detection Of Single DNA Molecules On Microchips," Analytical Chemistry, vol. 69 No. 17, pp. 3451-3457, Sep. 1, 1997.

Effenhauser, Carlo S. et al., "Integrated Chip-Based Capillary Electrophoresis," Electrophoresis, vol. 18, pp. 2203-2213, 1997.

Ericson, Christer et al., "Electroosmosis- and Pressure-Driven Chromatography In Chips Using Continuous Beds," Analytical Chemistry, vol. 72, No. 1, pp. 81-87, Jan. 1, 2000.

Fahrenberg, J. et al., "A Microvalve System Fabricated By Thermoplastic Molding," J. Micromech. Microeng., vol. 5, pp. 169-171, 1995.

Fettinger, J. C. et al., "Stacked Modules For Micro Flow Systems In Chemical Analysis: Concept And Studies Using An Enlarged Model," Sensors and Actuators B, vol. 17, pp. 19-25, 1993.

Figeys, Daniel et al., "An Integrated Microfluidics-Tandem Mass Spectrometry System For Automated Protein Analysis," Analytical Chemistry, vol. 70, No. 18, pp. 3728-3734, Sep. 15, 1998.

Figeys, Daniel et al., "Nanoflow Solvent Gradient Delivery From A Microfabricated Device For Protein Identifications By Electrospray Ionization Mass Spectrometry," Analytical Chemistry, vol. 70, No. 18, pp. 3721-3727, Sep. 15, 1998.

Folch, A. et al., "Molding Of Deep Polydimethylsiloxane Microstructures For Microfluidics And Biological Applications," Journal of Biomechanical Engineering, vol. 121, pp. 28-34, Feb. 1999.

Fu, Anne Y. et al., "A Microfabricated Fluorescence-Activated Cell-Sorter," Nature Biotechnology, vol. 17, pp. 1109-1111, Nov. 1999.

Galambos, Paul et al., "Electrical And Fluidic Packaging Of Surface Micromachined Electro-Microfluidic Devices," 8 pages, no date.

Gass, V. et al., "Integrated Flwo-Regulated Silicon Micropump," Sensors and Actuators A, vol. 43, pp. 335-338, 1994.

Gerlach, Torsten, "Pumping Gases By A Silicon Micro Pump With Dynamic Passive Valves," Transducers '97, 1997 International Conference on Solid-State Sensors and Actuators, Chicago, Illinois, pp. 357-360, Jun. 16-19, 1997.

Goll, C. et al., "Microvalves With Bistable Buckled Polymer Diaphragms," J. Micromech. Microeng., vol. 6, pp. 77-79, 1996.

Gravesen, Peter et al., "Microfluidics-A Review," J. Micromech. Microeng., vol. 3, pp. 168-192, 1993.

Greene, Chana, "Characterizing The Properties Of PDMS," pp. 1-11, Summer 2000.

Guérin, L. J. et al., "Simple And Low Cost Fabrication Of Embedded Micro-Channels By Using A New Thick-Film Photoplastic," Transducers '97, 1997 International Conference on Solid-State Sensors and Actuators, Chicago, Illinois, pp. 1419-1422, Jun. 18-19, 1997.

Harrison, D. Jed et al., "Micromachining A Miniaturized Capillary Eletrophoresis-Based Chemical Analysis System On A Chip," Science, vol. 261, pp. 895-897, Aug. 13, 1993.

Henion, Jack et al., "Capillary Electrophoresis/Mass Spectrometry: From One Meter Capillaries To Chip-Based Devices," 2 pages, 1999.

Hicks, Jennifer, "Genetics And Drug Discovery Dominate Microarray Research," R&D Magazine, pp. 28-33, Feb. 1999.

Hopfgartner, Gerard et al., "Exact Mass Measurement Of Product Ions For The Structural Elucidation Of Drug Metabolites With A Tandem Quadrupole Orthogonal-Acceleration Time-Of-Flight Mass Spectrometer," Journal of The American Society for Mass Spectrometry, vol. 10, pp. cover, 1305-1314, Dec. 1999.

Hornbeck, Larry J. et al., "Bistable Deformable Mirror Device," Spatial Light Modulators and Applications 1988 Technical Digest Series, Summaries of papers presented at the Spatial Light Modulators and Applications Topical Meeting, Optical Society of America, vol. 8, Postconference Edition, A215, pp. 107-110, Jun. 15-17, 1988.

Hosokawa, Kazuo et al., "Droplet-Based Nano/Picoliter Mixer Using Hydrophobic Microcapillary Vent," 1999 IEEE International Conference on Micro Electro Mechanical Systems, Technical Digest, pp. 388-393, 1999.

Hosokawa, Kazuo et al., "Handling Of Picoliter Liquid Samples In A Poly(dimethylsiloxane)-Based Microfluidic Device," Analytical Chemistry, vol. 71, No. 20, pp. 4781-4785, Oct. 15, 1999.

Ikuta, Koji et al., "Three Dimensional Micro Integrated Fluid Systems (MIFS) Fabricated By Stereo Lithography," IEEE, pp. 1-6, 1994.

Jacobson, Stephen C. et al., "High-Speed Separations On A Microchip," Analytical Chemistry, vol. 66, No. 7, pp. 1114-1118, Apr. 1, 1994.

Jacobson, Stephen C. et al., "Microfluidic Devices For Electrokinetically Driven Parallel And Serial Mixing," Analytical Chemistry, vol. 71, No. 20, pp. 4455-4459, Oct. 15, 1999.

Jerman, Hal, "Electrically-Activated, Normally-Closed Diaphragm Valves," Transducers '91, 1991 International Conference on Solid-State Sensors and Actuators, pp. cover, 1045-1048, 1991.

Jo, Byung-Ho et al., "Fabrication Of Three-Dimensional Microfluidic Systems By Stacking Molded Polydimethylsiloxane (PDMS) Layers" SPIE, vol. 3877, pp. 222-229, Sep. 1999.

Jo, Byung-Ho et al., "Three-Dimensional Micro-Channel Fabrication In Polydimethylsiloxane (PDMS) Elastomer," Journal of Microelectromechanical Systems, vol. 9, No. 1, pp. 76-81, Mar. 2000.

Jung, D. R. et al., "Chemical And Physical Interactions At Metal/Self-Assembled Organic Monolayer Interfaces," pp. 1-54, 1994.

Kagen, C. R., "Organic-Inorganic Hybrid Materials As Semiconducting Channels In Thin-Film Field-Effect Transistors," Science, vol. 286, pp. 945-947, Oct. 29, 1999.

Kapur, Ravi et al., "Fabrication And Selective Surface Modification Of 3-Dimensionally Textured Biomedical Polymers From Etched Silicon Substrates," Journal of Biomedical Meterials Research, vol. 33, pp. 205-216, 1996.

Kawano, Yasushi et al., "Rapid Isolation And Identification Of Staphylococcal Exoproteins By Reverse Phase Capillary High Performance Liquid Chromatography-Electrospray Ionization Mass Spectrometry," FEMS Microbiology Letters, vol. 189, pp. 103-108, 2000.

Kenis, Paul J. A. et al., "Microfabrication Inside Capillaries Using Multiphase Laminar Flow Patterning," Science, vol. 285, pp. 83-85, Jul. 2, 1999.

Khoo, Melvin et al., "A Novel Micromachined Magnetic Membrane Microfluid Pump," pp. 1-4, no date.

Kim, Enoch et al., "Micromolding In Capillaries: Applications In Materials Science," J. Am. Chem. Soc., vol. 118, No. 24, pp. 5722-5731, 1996.

Kim, Enoch et al., "Polymer Microstructures Formed By Moulding In Capillaries," Nature, vol. 376, pp. 581-584, Aug. 17, 1995.

Kopp, Martin U. et al., "Chemical Amplification: Continuous-Flow PCR On A Chip," Science, vol. 280, pp. 1046-1048, May 15, 1998.

Kuhn, Lawrence et al., "Silicon Charge Electrode Array For Ink Jet Printing," IEEE Transactions on Electron Devices, vol. ED-25, No. 10, pp. 1257-1260, Oct. 1978.

Kumar, Amit et al., "Features Of Gold Having Micrometer To Centimeter Dimensions Can Be Formed Through A Combination Of Stamping With An Elastomeric Stamp And An Alkanethiol 'Ink' Followed By Chemical Etching," Appl. Phys. Lett., vol. 63, No. 14, pp. 2002-2004, Oct. 4, 1993.
Kumar, Amit et al., "Patterning Self-Assembled Monolayers: Applications In Materials Science," Langmuir, vol. 10, pp. 1498-1511, 1994.
Lagally, Eric T. et al., "Monolithic Integrated Microfluidic DNA Amplification And Capillary Electrophoresis Analysis System," Sensors and Actuators B, vol. 63, pp. 138-146, 2000.
Lammerink, T. S. J. et al., "Modular Concept For Fluid Handling Systems," IEEE, pp. 389-394, 1996.
Lazar, Iulia M. et al., "Novel Microfabricated Device For Electrokinetically Induced Pressure Flow And Electrospray Ionization Mass Spectrometry," Journal of Chromatography A, vol. 892, pp. 195-201, 2000.
Li, Jianjun et al., "Integration Of Microfabricated Devices To Capillary Electrophoresis-Electrospray Mass Spectrometry Using A Low Dead Volume Connection: Application To Rapid Analyses Of Proteolytic Digests," Analytical Chemistry, vol. 71, No. 15, pp. 3036-3045, Aug. 1, 1999.
Li, Paul C. H. et al., "Transport, Manipulation, And Reaction Of Biological Cells On-Chip Using Electrokinetic Effects," Analytical Chemistry, vol. 69, No. 8, pp. 1564-1568, Apr. 15, 1997.
Licklider, Larry et al., "A Micromachined Chip-Based Electrospray Source For Mass Spectrometry," Analytical Chemistry, vol. 72, No. 2, pp. 367-375, Jan. 15, 2000.
Lin, L. Y. et al., "Free-Space Micromachined Optical Switches For Optical Networking," IEEE Journal of Selected Topics in Quantum Electronics, vol. 5, No. 1, pp. 4-9, Jan. 1999.
Lin, Yuehe et al., "Laser Micromachined Isoelectric Focusing Device On Polymer Substrate For Electrospray Mass Spectrometry," SPIE, vol. 3877, pp. 28-35, Sep. 1999.
Liu, Hanghui et al., "Development Of Multichannel Devices With An Array Of Electrospray Tips For High-Throughput Mass Spectrometry," Analytical Chemistry, vol. 72, No. 14, pp. 3303-3310, Jul. 15, 2000.
Lötters, J C et al., "The Mechanical Properties Of The Rubber Elastic Polymer Polydimethylsiloxane For Sensor Application," J. Micromech. Microeng., vol. 7, pp. 145-147, 1997.
Lucy, Charles A. et al., "Characterization of the Cationic Surfactant Induced Reversal Of Electroosmotic Flow In Capillary Electrophoresis," Anal. Chem., vol. 68, pp. 300-305, 1996.
Maluf, N., "An Introduction To Microelectromechanical Systems Engineering," Artech House Publishers, Boston London, pp. 42-45, Dec. 1999.
Manz, A. et al. "Micromachining Of Monocrystalline Silicon and Glass For Chemical Analysis Systems," Trends in Analytical Chemistry, vol. 10, No. 5, pp. 114-149, 1991.
Marshall, Sid, "Fundamental Changes Ahead For Lab Instrumentation," R&D Magazine, 5 pages, Feb. 1999.
Marsili, Ray, "Lab-On-A-Chip Poised To Revolutionize Sample Prep," R&D Magazine, 5 pages, Feb. 1999.
Maule, John, "Pulsed-Field Gel Electrophoresis," Molecular Biotechnology, vol. 9, pp. 107-126, 1998.
McDonald, J. Cooper et al., "Fabrication Of Microfluidic Systems In Poly(dimethylsiloxane)," Electrophoresis, vol. 21, pp. 27-40, 2000.
Muller, Richard S. et al., "Surface-Micromachined Microoptical Elements And Systems," Proceedings of the IEEE, vol. 86, No. 8, pp. 1705-1720, Aug. 1998.
New Objective, Inc., "What Is Electrospray," www.newobjective.com/electrospray/electrospray.html, 4 pages, 1999.
Oleschuk, Richard D. et al., "Analytical Microdevices For Mass Spectrometry," Trends In Analytical Chemistry, vol. 19, No. 6, pp. 379-388, 2000.
Olsson, Anders et al., "Simulation Studies Of Diffuser and Nozzle Elements For Valve-Less Micropumps," Transducers '97, 1997 International Conference on Solid-State Sensors and Actuators, Chicago, Illinois, pp. 1039-1042, Jun. 16-19, 1997.
O'Reilly, Marie-Anne J. et al., "The Technique Of Pulsed Field Gel Electrophoresis And Its Impact On Molecular Immunology," Journal of Immunological Methods, vol. 131, pp. 1-13, 1990.
Pethig, Ronald et al., "Applications Of Dielectrophoresis In Biotechnology," Tibtech, vol. 15, pp. 426-432, Oct. 1997.

Protana website, "NanoES Products," www.protana.com/products/default.asp, 3 pages, Sep. 19, 2000.
Qin, Dong et al., "Elastomeric Light Valves," Adv. Mater., vol. 9, No. 5, pp. 407-410, 1997.
Qin, Dong et al., "Photolithograhy With Transparent Reflective Photomasks," J. Vac. Sci. Technol. B, vol. 16, No. 1, pp. 98-103, Jan. 1998.
Rapp, R. et al., "LIGA Micropump For Gases And Liquids," Sensors and Actuators A, vol. 40, pp. 57-61, Jan. 1994.
Roylance, Lynn Michelle et al., "A Batch-Fabricated Silicon Accelerometer," IEEE Transactions on Electron Devices, vol. ED-26, No. 12, pp. 1911-1917, Dec. 1979.
Sandia National Laboratories, "Electro Microfluidic Dual In-Line Package (EMDIP)," 2 pages, no date.
Sanjoh Akira et al., "Spatiotemporal Protein Crystal Growth Studies Using Microfluidic Silicon Devices," Journal of Crystal Growth, vol. 196, pp. 691-702, 1999.
Schasfoort, Richard B. M. et al., "Field-Effect Flow Control for Microfabricated Fluidic Networks," Science, vol. 286, pp. 942-945, Oct. 29, 1999.
Schomburg, W. K. et al., "Fabrication Of Polymer Microcomponents With The AMANDA-Process," New Materials and Directions, Eurosensors XII, pp. 711-714, Sep. 13-16, 1998.
Schueller, Olivier J. A. et al., "Fabrication Of Glassy Carbon Microstructures By Soft Lithography," Sensors and Actuators A, vol. 72, pp. 126-139, 1999.
Shevchenko, Andrej et al., "Rapid 'de Novo' Peptide Sequencing By A Combination Of Nanoelectrospry, Isotopic Labeling And A Quadrupole/Time-Of-Flight Mass Spectometer," Rapid Communications in Mass Spectrometry, vol. 11, pp. 1015-1024, 1997.
Shinohara, Jun et al., "A High Pressure-Resistance Micropump Using Active And Normally-Closed Valves," IEEE, pp. 86-91, 2000.
Shoji, Shuichi, "Fluids For Sensor Systems," Topics in Current Chemistry, vol. 194, pp. 163-188, 1998.
Shoji, Shuichi et al., "Smallest Dead Volume Microvalves For Integrated Chemical Analyzing Systems," Transducers '91, 1991 International Conference on Solid-State Sensors and Actuators, San Francisco, California, pp. cover, 1052-1055, 1991.
Smits, J. G., "Piezoelectric Micropump With Three Valves Working Peristaltically," Sensors and Actuators, vol. A21-A23, pp. 203-206, 1990.
Sohn, L. L. et al., "Capacitance Cytometry: Measuring Biological Cells One By One," PNAS, vol. 97, No. 20, pp. 10687-10690, Sep. 26, 2000.
Thompson, L. F. et al., "Introduction to Microlithography," 185th Meeting of the American Chemical Society, Seattle, WA, pp. 2 cover pages, 1-13, Mar. 20-25, 1983.
Todd, Paul et al., "Chapter 12—Cell Electrophoresis," Flow Cytometry and Sorting, John Wiley & Sons, pp. 5 cover pages and 217-229, 1979.
Tufte, O. N. et al., "Silicon Diffused-Element Piezoresistive Diaphragms," Journal of Applied Physics, vol. 33, No. 11, pp. 3322-3327, Nov. 1962.
Ullmann's Encyclopedia of Industrial Chemistry, Sections 6 to 6.3, Topic: Carbon Black, Sixth Edition, 7 pages, 1999.
Unger, Marc A. et al., "Monolithic Microfabricated Valves And Pumps By Multilayer Soft Lithography," Science, vol. 288, pp. 113-116, Apr. 7, 2000.
Van De Pol, F.C.M. et al., "A Thermo-Pneumatic Actuation Principle For A Microminiature Pump And Other Micromechanical Devices," Sensors and Actuators, vol. 17, Nos. 1-2, pp. 139-143, May 3, 1989.
Van De Pol, F.C.M. et al., "Micro Liquid Handling Devices—A Review," Micro Systems Technologies, vol. 90, pp. 799-805, 1990.
Van Den Berg, A. et al., "Micro Total Analysis Systems," Proceedings of the μTAS '94 Workshop, University of Twente, The Netherlands, 17 pages, Nov. 21-22, 1994.
Verpoorte, Elisabeth M. J. et al., "Three-Dimensional Micro Flow Manifolds For Miniaturized Chemical Analysis Systems," J. Micromech. Microeng., vol. 7, pp. 246-256, 1994.
Vieider, Christian et al., "A Pneumatically Actuated Micro Valve With A Silicon Rubber Membrane For Integration With Fluid Handling Systems," Transducers '95, 8th International Conference on Solid-State Sensors and Actuators and Eurosensors IX, Stockholm, Sweden, pp. 284-286, Jun. 25-29, 1995.

Volkmuth, W. D. et al., "DNA Electrodiffusion In A 2D Array Of Posts," Physical Review Letters, vol. 72, No. 13, pp. 2117-2120, Mar. 28, 1994.

Volkmuth, W. D. et al., "DNA Electrophoresis In Microlithographic Arrays," Nature, vol. 358, pp. 600-602, Aug. 13, 1992.

Washizu, Masao et al., "Molecular Dielectrophoresis Of Biopolymers," IEEE Transactions on Industry Applications, vol. 30, No. 4, pp. 835-843, Jul. 1994.

Wilbur, James L. et al., "Lithographic Molding: A Convenient Route To Structures With Sub-Micrometer Dimensions," Adv. Mater., vol. 7, No. 7, pp. 649-652, 1995.

Wilm, Matthias et al., "Femtomole Sequencing Of Proteins From Polyacrylamide Gels By Nano-Electrospray Mass Spectrometry," Nature, vol. 379, pp. 466-469, Feb. 1, 1996.

Xia, Younan et al., "Complex Optical Surfaces Formed by Replica Molding Against Elastomeric Masters," Science, vol. 273, pp. 347-349, Jul. 19, 1996.

Xia, Younan et al., "Micromolding Of Polymers In Capillaries: Applications In Microfabrication," Chem. Mater., vol. 8, No. 7, pp. 1559-1566, 1996.

Xia, Younan et al., "Reduction In The Size Of Features Of Patterned SAMs Generated By Microcontact Printing With Mechanical Compression Of The Stamp," Adv. Mater., vol. 7, No. 5, pp. 471-473, 1995.

Xia, Younan et al., "Soft Lithography," Angew. Chem. Int. Ed., vol. 37, pp. 551-575, 1998.

Xu, Bing et al., "Making Negative Poisson's Ratio Microstructures By Soft Lithography," Adv. Mater., vol. 11, No. 14, pp. 1186-1189, 1999.

Xu, Jingdong et al., "Room-Temperature Imprinting Method For Plastic Microchannel Fabrication," Analytical Chemistry, vol. 72, No. 8, pp. 1930-1933, Apr. 15, 2000.

Xue, Qifeng et al., "Integrated Multichannel Microchip Electrospray Ionization Mass Spectrometry: Analysis Of Peptides From On-Chip Tryptic Digestion of Melittin," Rapid Communications In Mass Spectrometry, vol. 11, 1253-1256, 1997.

Xue, Qifeng et al., "Multichannel Mircochip Electrospray Mass Spectrometry," Analytical Chemistry, vol. 69, No. 3, pp. 426-430, Feb. 1, 1997.

Yang, Xing et al., "A Low Power MEMS Silicon/Parylene Valve," Solid-State Sensor and Actuator Workshop, Hilton Head Island, South Carolina, 4 pages, Jun. 7-11, 1998.

Yang, Xing et al., "A MEMS Thermopneumatic Silicone Membrane Valve," IEEE 10th Annual International Workshop of Micro Electro Mechanical Systems, Nagoya, Japan, pp. cover, 114-118, Jan. 26-30, 1997.

Yazdi, Navid et al., "Micromachined Inertial Sensors," Proceedings of IEEE, vol. 86, No. 8, pp. 1640-1659, Aug. 1998.

Young, A. M. et al., "Contoured Elastic-Membrane Microvalves For Microfluidic Network Integration," Journal of Biomechanical Engineering, vol. 121, pp. 2-6, Feb. 1999.

Zengerle, R. et al., "A Micro Membrane Pump With Electrostatic Actuation," Micro Electro Mechanical Systems '92, Travemünde, Germany, pp. 19-24, Feb. 4-7, 1992.

Zengerle, R. et al., "Performance Simulation Of Microminiaturized Membrane Pumps," 7th International Conference on Solid-State Sensors and Actuators, Yokohama, Japan, pp. 2 cover pages, 106-109, Jun. 7-10, 1993.

Zhang, B. et al., "Microfabricated Devices For Capillary Electrophoresis-Electrospray Mass Spectrometry," Analytical Chemistry, vol. 71, No. 15, pp. 3258-3264, Aug. 1, 1999.

Affholter, Joseph et al., "Engineering A Revolution," Chemistry in Britain, pp. 48-51, Apr. 1999.

Arnold, Frances H., "Design By Directed Evolution," Accounts of Chemical Research, vol. 31, No. 3, pp. 125-131, 1998.

Ashkin, A. et al., "Optical Trapping And Manipulation Of Single Cells Infrared Laser Beams," Nature, vol. 330, No. 24, pp. 769-771, Dec. 31, 1987.

Ashkin, A. et al., "Optical Trapping And Manipulation Of Viruses And Bacteria," Science, vol. 235, pp. 1517-1520, Mar. 20, 1987.

Barron, Annelise E. et al., "Capillary Electrophoresis Of DNA In Uncross-Linked Polymer Solutions," Journal of Chromatography A, vol. 652, pp. 3-16, 1993.

Barron, Annelise E. et al., "DNA Separations By Slab Gel And Capillary Electrophoresis - Theory And Practice," Separation and Purification Methods, vol. 24, No. 1, pp. 1-118, 1995.

Barron, Annelise E. et al., "The Use Of Coated And Uncoated Capillaries For The Electrophoretic Separation Of DNA In Dilute Polymer-Solutions," Electrophoresis, vol. 16, pp. 64-74, 1995.

Belgrader, Phillip et al., "Rapid Pathogen Detection Using A Microchip PCR Array Instrument," Clinical Chemistry, vol. 44, No. 10, pp. 2191-2194, 1998.

Blanch, Harvey W. et al., Biochemical Engineering, pp. 2 cover pages and 305, 1996.

Blankenstein, Gert et al., "Modular Concept Of A Laboratory On A Chip for Chemical And Biochemical Analysis," Biosensors & Bioeletronics, vol. 13, No. 3-4, pp. 427-438, 1998.

Brush, Michael, "Automated Laboratories," The Scientist, vol. 13, No. 4, 10 pages, Feb. 15, 1999.

Budowle, Bruce et al., "Analysis Of The VNTR Locus DIS80 By The PCR Followed By High-Resolution PAGE," Am. J. Hum. Genet., vol. 48, pp. 137-144, 1991.

Buican, Tudor N. et al., "Automated Single-Cell Manipulation And Sorting By Light Trapping," Applied Optics, vol. 26, No. 24, pp. 5311-5316, Dec. 15, 1987.

Burbaum, Jonathan J. et al., "New Technologies For High-Throughput Screening," Current Opinion in Chemical Biology, vol. 1, pp. 72-78, 1997.

Busch, J. et al., Methods For The Differentiation Of Microorganisms, Journal of Chromatography B, vol. 722, pp. 263-278, 1999.

Cai, Weiwen, et al., "High-Resolution Restriction Maps Of Bacterial Artificial Chromosomes Constructed By Optical Mapping," Proc. Natl. Acad. Sci. USA, vol. 95, pp. 3390-3395, Mar. 1998.

Castro, Alonso et al., "Fluorescene Detection And Size Measurement Of Single DNA Molecules," Analytical Chemistry, vol. 65, No. 7, pp. 849-852, Apr. 1, 1993.

Chiu, Chi-Sung et al., "Single Molecule Measurements Calibrate Green Fluorescent Protein Surface Densities On Transparent Beads For Use With 'Knock-In' Animals And Other Expression Systems," Journal of Neuroscience Methods, vol. 105, pp. 55-63, 2001.

Chou, Hou-Pu et al., "Disposable Microdevices For DNA Analysis And Cell Sorting," Proc. Solid-State Sensor and Actuator Workshop, Hilton Head, South Carolina, pp. 11-14, Jun. 8-11, 1998.

Chou, Hou-Pu et al., "Microfabricated Devices For Sizing DNA And Sorting Cells," Micro- and Nanofabricated Structures and Devices for Biomedical Environmental Applications, Proceedings of SPIE, vol. 3258, pp. 181-187, 1998.

Costerton, J. William et al., "Microbial Biofilms," Annu. Rev. Microbiol., vol. 49, pp. 711-745, 1995.

Cowen, S. et al., "An On-Chip Miniature Liquid Chromatography System: Design, Construction And Characterization," Micro Total Analysis Systems, Proceedings of the µTAS '94 Workshop, University of Twente, The Netherlands, pp. 2 cover pages and 295-298, 1995.

Crosland-Taylor, P.J., "A Device For Counting Small Particles Suspended In A Fluid Through A Tube," Nature, vol. 171, pp. 37-38, Jan. 3, 1953.

Delisa, Matthew P. et al., "Mapping Stress-Induced Changes In Autoinducer AI-2 Production In Chemostat-Cultivated *Escherichia coli* K-12," Journal of Bacteriology, vol. 183, No. 9, pp. 2918-2928, May 2001.

Effenhauser, Carlo S. et al., "Miniaturizing A Whole Analytical Laboratory Down To Chip Size," American Laboratory, vol. 26, No. 14, pp. cover, 15, 16, 18, 1994.

Effenhauser, Carlo S., "Integrated Chip-Based Microcolumn Separation Systems," Topics in Current Chemistry, vol. 194, pp. cover, 52-82, 1998.

Felix, Arthur M. et al., "Pegylated Peptides IV - Enhanced Biological Activity Of Site-Directed Pegylated GRF Analogs," International Journal of Peptide & Protein Research, vol. 46, pp. 253-264, 1995.

Felix, Arthur M., "Site-Specific Poly (ethylene glycol)ylation of Peptides," Poly(Ethylene Glycol) Chemistry and Biological Applications, ACS Symposium Series 680, pp. 2 cover pp., 218-238, 1997.

Fiedler, Stefan et al., "Dielectrophoretic Sorting Of Particles And Cell In A Microsystem," Analytical Chemistry, vol. 70, No. 9, pp. 1909-1915, May 1, 1998.

Fu, Anne Y. et al., "An Integrated Microfabricated Cell Sorter," Analytical Chemistry, vol. 74, No. 11, pp. 2451-2457, Jun. 1, 2002.

Fulwyler, M. J., "Electronic Separation Of Biological Cells By Volume,"Science, pp. 910-911, Nov. 1965.

Geng, Xindu et al., "Retention Model For Proteins In Reversed-Phase Liquid Chromatography," Journal of Chromatography, vol. 296, pp. 15-30, 1984.

Ginsberg, Michael A., "New Laser System Measure DNA Fragments," Biophotonics International, p. 20, Nov./Dec. 1996.

Giusti, Alan et al., "Application Of Deoxyribonucleic Acid (DNA) Polymorphisms To The Analysis Of DNA Recovered From Sperm," Journal of Forensic Sciences, vol. 31, No. 2, pp. 409-417, Apr. 1986.

Gombotz, W. R. et al., "Pegylation: A Tool To Enhance Protein Delivery," Abstracts of Papers, American Chemical Society, vol. 217, Part 2, 2 pages, Mar. 21-25, 1999.

Gonzalez, Jesus E. et al., "Improved Indicators Of Cell Membrane Potential That Use Fluorescence Resonance Energy Transfer," Chemistry & Biology, vol. 4, No. 4, pp. 269-277, Apr. 1997.

Goodwin, Peter M. et al., "Rapid Sizing Of Individual Fluorescently Stained DNA Fragments By Flow Cytometry," Nucleic Acids Research, vol. 21, No. 4, pp. 803-806, 1993.

Guerra, Patricia I. et al., "PEGylation Prevents The N-Terminal Degradation Of Megakaryocyte Growth And Development Factor," Pharmaceutical Research, vol. 15, No. 12, pp. 1822-1827, 1998.

Hancock, Robert E.W., "A Brief On Bacterial Biofilms," Nature Genetics, vol. 29, p. 360, Dec. 2001.

Hanes, Jozef, et al., " In Vitro Selection And Evolution Of Functional Proteins By Using Ribosome Display," Proc. Natl. Acad. Sci. USA, vol. 94, pp. 4937-4942, May 1997.

Harrison, D. Jed et al., "Integration Of Analytical Systems Incorporating Chemical Reactions And Electrophoretic Separation," Micro Total Analysis Systems, Proceedings of the µTAS '94 Workshop, University of Twente, The Netherlands, pp. 2 cover pages and 105-111, 1995.

Heo, Jinseok et al., "A Microfluidic Bioreactor Based On Hydrogel-Entrapped E. coli: Cell Viability, Lysis, And Intracellular Enzyme Reactions,"0 Analytical Chemistry, vol. 75, No. 1, pp. 22-26, Jan. 1, 2003.

Herbert, D. et al., "The Continuous Culture Of Bacteria; A Theoretical And Experimental Study," J. Gen. Microbiol., vol. 14, pp. 601-622, 1956.

Herbert, D., "Continuous Culture of Bacteria," The Journal of General Microbiology, vol. 15, pp. 2 cover pages and iv, 1956.

Herbert, D., "Continuous Culture Of Bacteria: Principles And Applications," Chemistry and Industry, pp. 381, Mar. 29, 1958.

Hermanson, Greg T. et al., "Chapter 2 - Activation Methods," Immobilized Affinity Ligand Techniques, Academic Press, pp. 2 cover pages, 51-136, 1992.

Hoffmuller, Ulrich et al., "In Vitro Evolution And Selection Of Proteins: Ribosome Display For Larger Libraries," Angew. Chem. Int. Ed., vol. 37, No. 23, pp. 3241-3243, 1998.

Jacobson, Ken et al., "International Workshop On The Application Of Fluorescence Photobleaching Techniques To Problems In Cell Biology," Federation Proceedings, vol. 42, No. 1, pp. 72-79, Jan. 1983.

Jacobson, Stephen C. et al., "Open Channel Electrochomatography On A Microchip," Analytical Chemistry, vol. 66, No. 14, pp. 2369-2373, Jul. 15, 1994.

Jannasch, H. W. et al., "Experimental Bacterial Ecology Studied In Continous Culture," Advances in Microbial Physiology, vol. 11, pp. cover and 165-212, 1974.

Jeffreys, Alec J. et al., "Hypervariable 'Minisatellite 'Regions In Human DNA," Nature, vol. 314, pp. 67-73, Mar. 7, 1985.

Jermutus, Lutz, et al., "Recent Advances In Producing And Selecting Functional Proteins By Using Cell-Free Translation," Current Opinion in Biotechnology, vol. 9, pp. 534-548, 1998.

Ju, Li-ya et al., "Application Of Silver Staining To The Rapid Typing Of The Polymorphism Of HLA-DQ Alleles By Enzymatic Amplification and Allele-Specific Restriction Fragment Length Polymorphism," Electrophoresis, vol. 12, pp. 270-273, 1991.

Kamentsky, Louis A. et al., "Spectrophotometer: New Instrument For Ultrarapid Cell Analysis," Science, vol. 150, pp. 630-631, Oct. 29, 1965.

Kanter, Evan et al., "Analysis Of Restriction Fragment Length Polymorphisms In Deoxyribonucleic Acid (DNA) Recovered From Dried Bloodstains," Journal of Forensic Sciences, vol. 31, No. 2, pp. 403-408, Apr. 1986.

Keller, Richard A. et al., "Single-Molecule Fluorescence Analysis In Solution," Applied Spectroscopy, vol. 50, No. 7, pp. 12A-30A, Jul. 1996.

Kodera, Yoh et al., "Pegylation Of Proteins And Bioactive Substances For Medical And Technical Applications," Prog. Polym. Sci., vol. 23, pp. 1233-1271, 1998.

Lane, P.G., "Analysis Of A Continuous-Culture Technique For The Selection Of Mutants Tolerant To Extreme Environmental Stress," Biotechnology and Bioengineering, vol. 65, No. 4, pp. 397-406, Nov. 20, 1999.

Lawrence, J. R. et al., "Optical Sectioning Of Microbial Biofilms," Journal of Bacteriology, vol. 173, No. 20, pp. 6558-6567, Oct. 1991.

Lee, L. Stanford et al., "Prolonged Circulating Lives Of Single-Chain Fv Proteins Conjugated With Polyethylene Glycol: A Comparison Of Conjugation Chemistries And Compounds," Bioconjugate Chem., vol. 10, pp. 973-981, 1999.

Lessard, Guillaume A. et al., "A Scanning Apertureless Fluorescence Microscope," 8 pages, 1999.

Levine, Leanna M. et al., "Measurement Of Specific Protease Activity Utilizing Fluorescence Polarization," Analytical Biochemistry, vol. 247, pp. 83-88, 1997.

Llopis, Juan et al., "Ligand-Dependent Interactions Of Coactivators Steroid Receptor Coactivator-1 And Peroxisome Proliferator-Activated Receptor Binding Protein With Nuclear Hormone Receptors Can Be Imaged In Live Cells And Are Required For Transcription," PNAS, vol. 97, No. 8, pp. 4363-4368, Apr. 11, 2000.

Maresova, H. et al., "A Chemostat Culture As A Tool For The Improvement Of A Recombinant E. coli Strain Over-Producing Penicillin G Acylase," Biotechnology And Bioengineering, vol. 75, No. 1, pp. 46-52, Oct. 5, 2001.

Mason, T. G. et al., "Shear Rupturing Of Droplets In Complex Fluids," Langmuir, vol. 13, pp. 4600-4613, 1997.

Mastrangelo, C. H. et al., "Vacuum-Sealed Silicon Micromachined Incandescent Light Source," IEDM, pp. 503-506, 1989.

Menchen, Steve et al., "Flowable Networks As DNA Sequencing Media In Capillary Columns," Electrophoresis, vol. 17, pp. 1451-1459, 1996.

Moldavan, Andrew, "Photo-Electric Technique For The Counting Of Microscopical Cells," Science, vol. 80, No. 2069, pp. 188-189, Aug. 24, 1934.

Monod, Jacques, "The Growth Of Bacterial Cultures," Annual Review of Microbiology, vol. III, pp. cover and 371-394, 1949.

Murray, Vincent et al., "Detection Of Polymorphisms Using Thermal Cycling With A Single Oligonucleotide On A DNA Sequencing Gel," Human Mutation, vol. 2, pp. 118-122, 1993.

Nagai, Yasuo et al., "A Fluorescent Inductor For Visualizing cAMP-Induced Phosphorylation In Vivo," Nature Biotechnology, vol. 18, pp. 313-316, Mar. 2000.

Nakamura, Yusuke et al., "Variable Number Of Tanden Repeat (VNTR) Markers For Human Gene Mapping," Science, vol. 235, pp. 1616-1622, Mar. 27, 1987.

Nielsen, Jens et al., Bioreaction Engineering Principles, Second Edition, pp. 2 cover pp. and 42-45, 2003.

Novivk, Aaron et al., "Description Of The Chemostat," Science, vol. 112, pp. 715-716, Dec. 15, 1950.

Novick, Aaron et al., "Experiments With The Chemostat On Spontaneous Mutations Of Bacteria," Proc. N. A. S., vol. 36, pp. 708-719, 1950.

Parker, Gregory J. et al., "Development Of High Throughput Screening Assays Using Fluorescence Polarization: Nuclear Receptor-Ligand-Binding And Kinase/Phophatase Assays," Journal of Biomolecular Screening, vol. 5, No. 2, pp. 77-88, 2000.

Petty, Jeffrey T. et al., "Characterization Of DNA Size Determination Of Small Fragments By Flow Cytometry," Anal. Chem., vol. 67, pp. 1755-1761, 1995.

Poplawski, M. E. et al., "A Simple Packaging Process For Chemical Sensors," Solid-State Sensor and Actuator Workshop, Hilton Head, South Carolina, pp. 25-28, Jun. 13-16, 1994.

Qu, Mingbo et al., "Toxicity And Biodegradation Of Formaldehyde In Anaerobic Methanogenic Culture," Biotechnology and Bioengineering, vol. 55, No. 5, pp. 727-736, Sep. 5, 1997.

Roberts, Richard W. et al., "RNA-Peptide Fusions For The In Vitro Selection Of Peptides And Proteins," Proc. Natl. Acad. Sci. USA, vol. 94, pp. 12297-12302, Nov. 1997.

Rotman, Boris, "A Simplified Device For Continuous Growth Of Microorganisms," Journal of Bacteriology, vol. 70, pp. 485-486, 1955.

Rouhi, Maureen, "Sizing, Sorting DNA One Piecce At A Time," C&EN, pp. 5-6, Jan. 11, 1999.

Samad, Akhtar et al., "Optical Mapping: A Novel, Single-Molecule Approach To Genomic Analysis," Genome Research, pp. 1-4, 1995.

Schwartz, David C., et al., "Optical Mapping Approaches To Molecular Genomics," Current Opinion in Biotechnology, vol. 8, pp. 70-74, 1997.

Seethala, Ramakrishna et al., "A Fluorescence Polarization Competition Immunoassay For Tyrosine Kinases," Analytical Biochemistry, vol. 255, pp. 257-262, 1998.

Shuler, Michael L. et al., "Chapter 6 - How Cells Grow," Bioprocess Engineering Basic Concepts, Second Edition, pp. 2 cover pp. and 155-200, 2002.

Sklar, Larry A. et al., Sample Handling For Kinetics And Molecular Assembly In Flow Cytometry, SPIE, vol. 3256, pp. 144-153, 1998.

Spicer, C. C., "The Theory Of Bacterial Constant Growth Apparatus," Biometrics, pp. 225-230, Jun. 1955.

Stemmer, Willem P.C. et al., "Rapid Evolution Of A Protein in vitro By DNA Shuffling," Nature, vol. 370, pp. 389-390, Aug. 4, 1994.

Swart, Remco et al., "Recent Progress In Open Tubular Liquid Chromatography," Trends in Analytical Chemistry, vol. 16, No. 6, pp. 332-342, 1997.

Sweet, Richard G., "Chapter 9 - Flow Sorters For Biologic Cells," Flow Cytometry and Sorting, John Wiley & Sons, pp. 5 cover pp. and 177-189, 1979.

Takahashi, Akiyuki et al., "Measurement Of Intracellular Calcium," Physiological Reviews, vol. 79, No. 4, pp. 1089-1125, Oct. 1999.

Tatari, Zohreh et al., "HLA-Cw Allele Analysis By PCR-Restriction Fragment Length Polymorphism: Study Of Known And Additional Alleies," Proc. Natl. Acad. Sci. USA, vol. 92, pp. 8803-8807, Sep. 1995.

Tawfik, Dan S. et al., "Man-Made Cell-Like Compartments For Molecular Evolution," Nature Biotechnology, vol. 16, pp. 652-656, Jul. 1998.

Taylor, Anne M. et al., "Microfluidic Multicompartment Device For Neuroscience Research," Lagmuir, vol. 19, pp. 1551-1556, 2003.

Terry, Stephen C. et al., "A Gas Chromatographic Air Analyzer Fabricated On A Silicon Wafer," IEEE Transactions on Electron Devices, vol. Ed-26, No. 12, pp. 1880-1886, Dec.1979.

Umdanhowar, P.B. et al., "Monodisperse Emulsion Generation Via Drop Break Off In A Coflowing Stream," Langmuir, vol. 16, pp. 347-351, 2000.

Unger, M et al., "Single-Molecule Fluorescence Observed With Mercury Lamp Illumination," Biotechniques, vol. 27, No. 5, pp. 1008-1014, Nov. 1999.

Vahey, Paul G. et al., "Development Of A Positive Pressure Driven Micro-Fabricated Liquid Chromatographic Analyzer Through Rapid-Prototyping With Poly(dimethylsiloxane) Optimizing Chromatographic Efficiency With Sub-Nanoliter Injections," Talanta, vol. 51, pp. 1205-1212, 2000.

Van Dilla, M. A. et al., "Cell Microfluorometry: A Method For Rapid Fluorescence Measurement," Science, vol. 163, pp. 1213-1214, Mar. 14, 1969.

Van Dilla, Marvin A. et al., "Chapter 2 - Introduction And Resume Of Flow Cytometry And Sorting," Flow Cytometry and Sorting, John Wiley & Sons, pp. 5 cover pp. and 11-37, 1979.

Veronese, F. M. et al., "Influence of PEGylation On The Release Of Low And High Molecular-Weight Proteins From PVA Matrices," Journal of Bioactive and Compatible Polymers, vol. 14, pp. 315-330, Jul. 1999.

Veronese, Francesco M., "Peptide And Protein PEGylation: A Review Of Problems And Solutions," Biomaterials, vol. 22, pp. 405-417, 2001.

Vogelstein, Bert et al., "Digital PCR," Proc. Natl. Acad. Sci. USA, vol. 96, pp. 9236-9241, Aug. 1999.

Ward, Keith B. et al., "Automatic Preparation Of Protein Crystals Using Laboratory Robotics And Automated Visual Inspection," Journal of Crystal Growth, vol. 90, pp. 325-339, 1988.

Webster, J.R. et a., "Monolithic Capillary Gel Electrophoresis Stage With On-Chip Detector," IEEE, pp. 491-496, 1996.

Whelen, A. Christian et al., "The Role Of Nucleic Acid Amplification And Detection In The Clinical Microbiology Laboratory," Annu. Rev. Microbiol., vol. 50, pp. 349-373, 1996.

Wiebe, Marilyn G. et al., "Evolution Of A Recombinant (Gucoamylase-Producing) Strain Of *Fusarium venenatum* A3/5 In Chemostat Culture," Biotechnology and Bioengineering, vol. 73, No. 2, pp. 146-156, Apr. 20, 2001.

Wu, Chunhung et al., "Viscosity-Adjustable Block Copolymer For DNA Separation By Capillary Electrophoresis," Electrophoresis, vol. 19, pp. 231-241, 1998.

Xu, Xiang et al., "Detection Of Programmed Cell Death Using Fluorescence Energy Transfer," Nucleic Acids Research, vol. 26, No. 8, pp. 2034-2035, 1998.

Yang, T. J. et al., "An Apertureless Near-Field Microscope For Fluorescence Imaging," Applied Physics Letters, vol. 76, No. 3, pp. 378-380, Jan. 17, 2000.

Yokobayashi, Yohei et al., "Evolutionary Design Of Genetic Circuits And Cell-Cell Communications," Advances in Complex Systems, vol. 6, No. 1, pp. 37-45, 2003.

Zaccolo, Manuela et al., "A Genetically Encoded, Fluorescent Indicator For Cyclic AMP In Living Cells," Nature Cell Biology, vol. 2, pp. 25-29, Jan. 2000.

Zalipsky, Samuel, "Chemistry Of Polyethyelene Glycol Conjugates With Biologically Active Molecules," Advanced Drug Delivery Reviews, vol. 16, pp. 157-182, 1995.

Zdeblick, Mark J. et al., "A Microminiature Electric-To-Fluidic Valve," Tranducers '87 , Proceedings of the 4th International Conference on Solid-State Sensors and Actuators, reprinted in Micromechanics and MEMS Classic and Seminal Papers to 1990, pp. 2 cover pp. 437-439, Jun. 1987.

MICROFLUIDIC-BASED ELECTROSPRAY SOURCE FOR ANALYTICAL DEVICES WITH A ROTARY FLUID FLOW CHANNEL FOR SAMPLE PREPARATION

FIELD OF THE INVENTION

This invention relates to microfluidic devices and methods for using the same. In particular, microfluidic devices of the present invention comprise a fluid flow channel and a means for providing a fluid sample from the fluid flow channel to an analytical device.

BACKGROUND OF THE INVENTION

Recently, microfluidic devices capable of conducting chemical reactions and assays on a single microchip have been developed. However, the method of detection has been mostly limited to laser-induced fluorescence (LIF) because of its simplicity and sensitivity. One of the limitations of LIF is that it requires the analyte of interest to be fluorescent. Since most compounds are not natural fluorophores, LIF is not an ideal detection method. Thus, in order to use LIF detection method, a derivatization step is often required to make compounds of interest amenable to LIF detection.

Mass spectrometry (MS) is currently being investigated as an alternative detection method for microfluidic devices. In this regard, electrospray ionization mass spectrometry (ESI-MS) is particularly suited due to the similarity in flow rates generated by the microchip (i.e., microfluidic device) with those required for ESI-MS. ESI-MS is a powerful tool that has been broadly applied to the structural analysis of biological molecules. In particular, it provides a facile means to interface liquid chromatographic (LC) systems and mass spectrometry (MS), creating a system that integrates separation with structural analysis and molecular identification. The development of LC-MS has revolutionized analytical chemistry and biochemistry.

In the post-genomic era, attention has turned from DNA sequencing to the more complex problem of analyzing how this genetic information directs cell function. The analysis of protein structure and function is one of the keys to this question. In particular, analysis methods currently under development are typically focused on identifying unknown proteins whose presence can be correlated with a function, disease state or reaction to potential drug candidates.

Mass spectrometry is a highly sensitive tool for the analysis of proteins. It enables the masses of fragment ions of proteins or peptides to be determined with high accuracy and with high sensitivity. High mass accuracy enables an accurate and specific sequencing of peptides. In combination with progress in genomic sequencing and bioinformatics, this enables the identification and characterization of unknown components of cells. In tandem with multidimensional gel electrophoresis methods, it provides a means to identify the complement of the proteins expressed by a cell under a defined set of conditions. This totality of expressed proteins is defined as the proteome.

Mass spectrometry is also developing from this simple "mining tool" for providing protein sequence information into more deeply integrated areas, such as functional characterization of biologically important genes, functional proteomics, quantitative mapping of cellular proteins and deciphering protein interaction networks. In addition to sequencing, mass spectrometry is currently the only tool available that can readily detect post-translational modifications (changes to protein structure after synthesis), such as phosphorylation and dephosphorylation and the actions of proteases that each plays critical roles in the control of cellular activity.

Another important MS application is the identification of molecules participating in the formation of macromolecular complexes. The study of molecular interactions is a rapidly developing field. The analysis of protein expression in cells (also known as proteomics) is therefore important in target identification and validation, and in ADME/PK (absorption-distribution-metabolism-excretion/pharmacokinetic) studies. However, such proteomic studies, in which proteins are identified by analysis of enzymatically produced peptide fragments, are expensive and labor-intensive. Technical difficulties exist in both sample separation and sample delivery systems for using ESI-MS in analysis of proteins, primarily because the samples that can be isolated from traditional gel-based electrophoresis are in very limited amounts. This makes them difficult to analyze in a traditional ESI-MS configuration.

To overcome some of the problems created by small sample sizes, interfaces capable of delivering low nanoliter per minute volumes of sample (so-called 'nanospray') to MS have been developed. These extend the time over which a very small amount of sample (e.g., 1 µL or less) can be delivered to the mass spectrometer, providing improved signal/noise ratios and thus sensitivity. However, Nano-ESI-MS is labor-intensive and slow (in current designs, sample loading and set-up of the electrospray capillary are both manual processes). In addition, it cannot be readily adapted to on-line capillary separation methods such as liquid chromatography or capillary electrophoresis. For these reasons, nanospray is most often used as a "static" or off-line method in which samples are analyzed one-at-a-time, representing a serious bottleneck in applications that requires high throughput. Software that integrates the variety of analytical methods required to perform high throughput analysis using these systems is already available, thus design of a robust multi-use interface is the bottleneck in adapting nanospray to high throughput applications.

Microfluidic device based electrospray sources for use in mass spectrometry have recently been developed; see for example, Oleschuk and Harrison, *Trends in Anal. Chem.*, 2000, 19, 379-388, and Licklider et al., *Anal. Chem.*, 2000, 72, 367-375. However, these methods utilize non-elastic microfluidic devices and require fabricating an electrospray nozzle directly on the microfluidic device or attaching a capillary electrospray emitter to the microfluidic device. Unfortunately, fabrication of an electrospray nozzle directly on the microfluidic device increases the manufacturing complexity, the production time and the cost. Methods for attaching a capillary electrospray emitter to current microfluidic devices also have severe limitations. For example, the junction between the microfluidic device and the electrospray nozzle emitter requires a tight seal to avoid fluid sample leakage. More significantly, it is difficult to attach an electrospray emitter to non-elastic microfluidic device without introducing a certain amount of void volume. Furthermore, the electrospray emitter must be carefully attached to the microfluidic device making mass production using batch processes difficult.

Moreover, in these microfluidic devices the flow of fluid is typically electroosmotically driven or by applying pressure directly on the inlet portion of the microfluidic devices. These fluid flow methods further limit the utility of these microchips. For example, use of electroosmotic flow is incompatibility with many buffer systems, may cause molecular dissociation, and molecules can be damaged or degraded due to exposure to electric fields. Most importantly the ionic buffers required to drive electroosmotic flow interfere with electrospray ionization and limit its usefulness. The use of electric fields is also incompatible applications that demand the use of non-aqueous solvents.

Therefore, there is a need for a microfluidic device which comprises a means for providing a sample of fluid to an analytical device which does not require fabrication of sample providing means directly on the microfluidic device??. There is also a need for a microfluidic device in which a readily available electrospray emitter can be easily attached. There is also a need for a microfluidic device which does not require electroosmotic flow or electrophoresis or a direct application of pressure on the inlet portion of the microfluidic device.

SUMMARY OF THE INVENTION

The present invention provides a microfluidic device comprising a means for providing a fluid sample from directly from the microfluidic device to an analytical device, and methods for using the same.

In one aspect, the present invention provides a microfluidic device comprising:

(a) a first elastic layer;
(b) a fluid flow channel within said elastic layer; and
(c) a means for providing a sample of fluid from said fluid flow channel to an analytical device.

In another aspect of the present invention, an analytical apparatus for analyzing a fluid sample is provided. The analytical apparatus comprises an analytical device for analyzing the fluid sample and the microfluidic device described above.

Yet another aspect of the present invention is a method for producing a microfluidic device comprising a means for introducing a fluid sample into an analytical device. The method generally comprises the steps of:

(a) producing a first elastic layer of the microfluidic device, wherein the first elastic layer comprises a fluid flow channel; and
(b) integrating a proximal end of a capillary within said fluid flow channel, wherein a distal end of said capillary comprises said sample introducing means.

Still another aspect of the present invention provides a method for analyzing a fluid sample using an analytical device comprising the steps of:

(a) introducing the fluid sample into the analytical device through a fluid flow channel of a microfluidic device, wherein the fluid flow channel is located within a first elastic layer of the microfluidic device; and
(b) analyzing said fluid sample using the analytical device.
Preferably, the analytical device is a mass spectrometer.

Preferably, the microfluidic device of the present invention further comprises a second elastic layer which is positioned on top of the first elastic layer. In one embodiment of the present invention, the second elastic layer comprises a pressure channel which can act as pumps and valves for controlling the flow of fluid within the fluid flow channel in the first elastic layer. Thus, microfluidic devices of the present invention have significant advantages in both the sample preparation and sample delivery (in scales of nL/min). For example, in sample preparation, the combination of miniaturized valves and pumps on top of the first elastic layer allows one to conduct complex sample preparation processes, thereby circumventing shortcomings (some of which are described above) of electroosmotically driven microfluidic devices.

Other benefits of microfluidic devices of the present invention include reduced manufacturing and operating costs, reduced resource consumption, reduced waste production, and increased throughput (e.g., both by speeding up sequential, individual runs and also by implementing parallel processing). Further advantages of microfluidic devices of the present invention include adaptation of traditional LC packing materials that enable separations to be permitted on the device. The revolutionized sample processing and biochemical analysis provided by the present invention create "flow" or on-line systems, which can be adapted to high throughput methods.

Thus, in one particular embodiment of the present invention, an integrated system of microfluidic device and ESI-MS (i.e., chip-ESI-MS) is used to process and then deliver nanoliter or picoliter scale samples with a uniform low sample flow rate (e.g., nL/min) for direct analysis of the fluid sample which has been prepared using the microfluidic device.

DEFINITIONS

The term "elastic layer" and "elastomeric later" are used interchangeably herein and refer to a material which can be deformed by applying pressure. Preferably, the Young's modulus of the elastic layer is from about 1 Pa to about 1 TPa, preferably from about 10 Pa to about 100 GPa, more preferably from about 20 Pa to about 1 GPa, still more preferably from about 50 Pa to about 10 MPa, and most preferably between about 100 Pa to about 1 MPa. However, elastomeric materials having a Young's modulus outside of these ranges can also be utilized depending on the needs of a particular application.

Unless otherwise stated, the term "liquid chromatography device" includes low pressure liquid chromatography devices (LPLC), medium pressure liquid chromatography devices (MPLC), and high pressure liquid chromatography devices (HPLC).

Unless otherwise stated, the term "electrospray mass spectrometer" refers to electrospray ionization mass spectrometers, including nanoelectrospray mass spectrometers.

The term "electrospray" refers to a method of generating a very fine liquid aerosol (i.e., mist) through electrostatic charging. Such methods are well known to one of ordinary skill in the art. Briefly, a plume of liquid droplets is generated by electrically charging a volume of liquid to a high voltage. The liquid becomes unstable as it is forced to hold more and more charge. When the liquid reaches a critical point (i.e., at critical charge/volume ratio), at which it can hold no more electrical charge, it rapidly dissociates (i.e., blows apart) into a cloud of tiny, highly charged "daughter" droplets. These tiny daughter droplets then fly towards detector which typically has opposite charge or ground potential. As droplets fly about, solvent molecules evaporate from their surface and the daughter droplets can further dissociate due to increased charge/volume ratio.

The term "nanoelectrospray mass spectrometer" refers to mass spectrometers having a low sample fluid flow rate. Nanoelectrospray mass spectrometers have sample fluid flow rate in the range of from about 1 nL/min to about 150 nL/min, and preferably from about 20 nL/min to about 50 nL/min.

The term "directly" as used in reference delivering or introducing a fluid sample from a microfluidic device to an analytical sample refers to a method for introducing a fluid sample to an analytical device without any intervening manual manipulation of the fluid sample. In particular the fluid sample leaving the microfluidic device enters the injection port of the analytical device directly.

The term "circular cross-section" refers to the cross-section of a channel that is a circle, oval, ellipse, or other similarly circular shape.

The term "capillary nozzle" refers to a device which has a capillary tube or similar opening which is used to provide a fluid sample from the microfluidic device to the analytical device. The tip of a capillary nozzle can be tapered or non-tapered. Preferably, the inner diameter of the capillary nozzle is from about 1 μm to about 100 μm, more preferably from about 10 μm to about 50 μm, and most preferably from about 10 μm to about 20 μm.

The term "integrated" refers to combining a microfluidic device with a means for fluid sample delivery such that the fluid sample is introduced directly to the sample injection site of the analytical device from the microfluidic device.

The term "analyte" refers to a particular compound which is to be analyzed by the analytical device.

The terms "injected" and "introduced" are used interchangeably herein and refer to providing the fluid sample into the analytical device for analysis.

The term "rotary" refers to a configuration in the fluid flow channel which allows circulation of a fluid within a confined region or section of the fluid flow channel.

The term "channel" refers to an empty space within the elastomeric layer in which a fluid can be introduced. Preferably, a liquid is introduced in a fluid channel and a gas is introduced in a pressure channel.

DETAILED DESCRIPTION

Figure 1A:
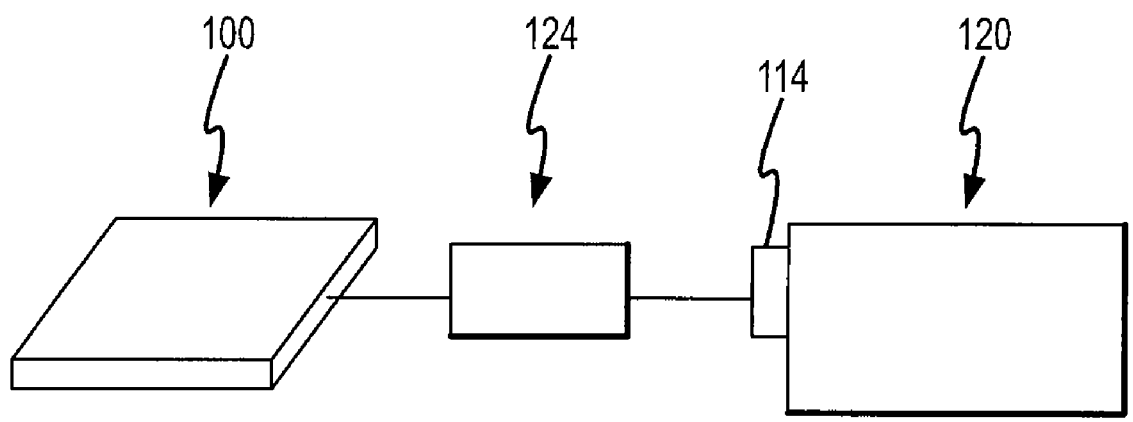
FIG. 1A is a schematic illustration of a microfluidic device comprising a means for delivering a fluid sample directly to an injection port of an analytical device.
Figure 1B:
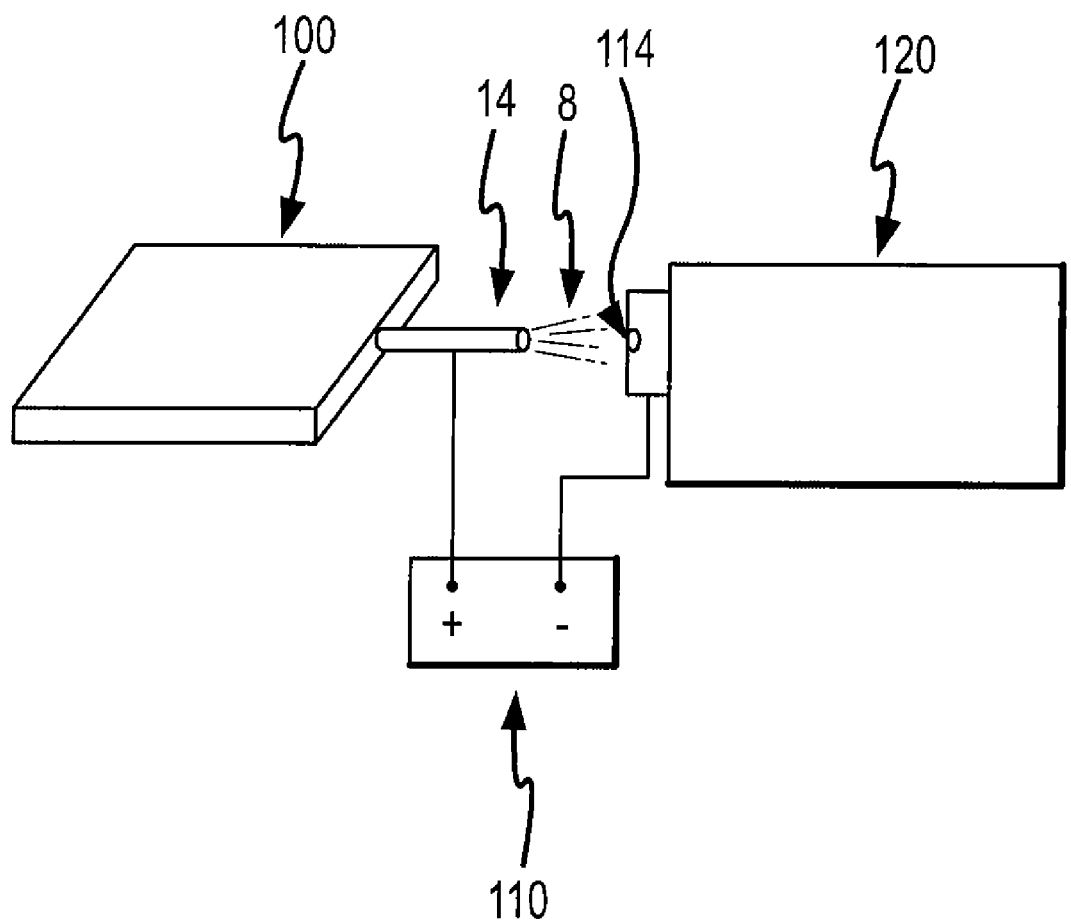
FIG. 1B is a schematic illustration of an analytical apparatus comprising a microfluidic device having an electrospray capillary interconnected to a mass spectrometer.

The present invention will be described with regard to the accompanying drawings which assist in illustrating various features of the invention. In this regard, the present invention generally relates to a microfluidic device comprising a means for providing a fluid sample from to an analytical device, an analytical apparatus comprising the same, and methods for using the same. The same numbers in different drawings represent identical elements. The drawings are provided for the purpose of illustrating the practice of the present invention and do not constitute limitations on the scope thereof.

The analytical device 120 can be any device which is used for analyzing a chemical compound. Typically the analytical device 120 has a sample injection port 114 for introducing a sample to be analyzed. While the sample can be in a pure form (i.e., neat), microfluidic devices of the present invention are particularly useful for analyzing compounds which are in a solution.

Preferably, the analytical device 120 is selected from the group consisting of UV spectrometers, fluorescence spectrometers, IR spectrometers, gas chromatographic devices, liquid chromatographic devices, NMR devices, mass spectrometers and combinations thereof. More preferably, the analytical device 120 is a mass spectrometer. And most preferably, the analytical device 120 is an electrospray mass spectrometer.

The fluid sample providing means 124 can include any device that allows delivery of the fluid sample from the microfluidic device 100 to the analytical device 120. Exemplary fluid sample delivery devices include the outlet ports of fluid flow channel on microfluidic devices; capillary nozzles (such as electrospray nozzles); needles, and Preferably, the fluid sample device is a capillary nozzle, and more preferably an electrospray nozzle.

Microfluidic devices of the present invention are capable of delivering a very minute amounts of samples to the analytical device, thereby increasing the sensitivity of the analytical device 120. In particular, microfluidic devices of the present invention are capable of providing a fluid sample to the analytical device at a flow rate of from about 1 nL/min to about 200 nL/min, preferably from about 10 nL/min to about 50 nL/min, and more preferably from about 10 nL/min to about 20 nL/min.

While the present invention is generally described in reference to microfluidic devices for preparing and/or providing fluid samples to electrospray mass spectrometers, it should be appreciated that the present invention is not limited to such.

For example, microfluidic devices of the present invention can be integrated with a LC-mass spectrometer, GC-mass spectrometer, liquid chromatography devices, gas chromatography devices, IR spectrometer, UV spectrometer, fluorescence spectrometer, or the like by using a capillary nozzle, needle, or some other fluid sample delivery means which provide a non-aerosol (i.e., mist) liquid samples to analytical devices.

One aspect of the present invention provides a microfluidic device 100 comprising a first elastic layer 25, a fluid flow channel 18 within the first elastic layer 25, and a means for providing a sample of fluid 124, preferably directly, from the fluid flow channel to an analytical device 120. Methods for producing microfluidic devices comprising an elastic layer is generally described in U.S. patent application Ser. No. 09/605,520, filed on Jun. 27, 2000. The first elastic layer 25 of microfluidic devices of the present invention preferably comprises at least two elastic portions, a top portion 20 and a bottom portion 10. In this embodiment, the fluid flow channel 18 is formed at the interface of the top arid bottom portions of the first elastic layer. This is particularly advantageous when forming a fluid flow channel having a circular cross-section for integrating a fluid sample providing means which comprises a capillary nozzle or other devices having a circular or rounded cross-section.

Preferably the inner diameter of the capillary nozzle 14 is from about 1 μm to about 100 μm, more preferably from about 10 μm to about 50 μm, and most preferably from about 10 μm to about 20 μm. The outer diameter of the capillary nozzle 14 is dependent on the width (e.g., diameter) of the fluid flow channel 18 or the portion of fluid flow channel which is integrated with the capillary nozzle.

It is preferred that the inner diameter of the capillary nozzle 14 be substantially similar to the width of fluid flow channel 18, as this diameter to width matching allows minimal fluid flow disruption and/or pressure differential between the fluid flow channel 18 and the capillary nozzle 14. Typically, the outer diameter of the capillary nozzle 14 is larger than the width of fluid flow channel 18; therefore, in order to provide a substantially similar width, the portion of fluid flow channel 18 which integrates the capillary nozzle 14 is constructed such that its width is substantially similar to the outer diameter of the capillary nozzle 14. It is preferred, however, that the volume of the portion of fluid flow channel 18 that integrates the capillary nozzle 14 be slightly smaller than the volume occupied by the outer dimension of the portion of capillary nozzle, as this arrangement provides a "snug" fit or a hermetic seal. This is particularly useful in microfluidic devices of the present invention as they have an elastic layer which can expand to accommodate the capillary nozzle 14. It should be appreciated that the amount of expansion possible by the first elastic layer depends on the particular nature of the material used. Alternatively, an adhesive can be used to secure the capillary 14 within the flow channel 18.

Figure 4A:
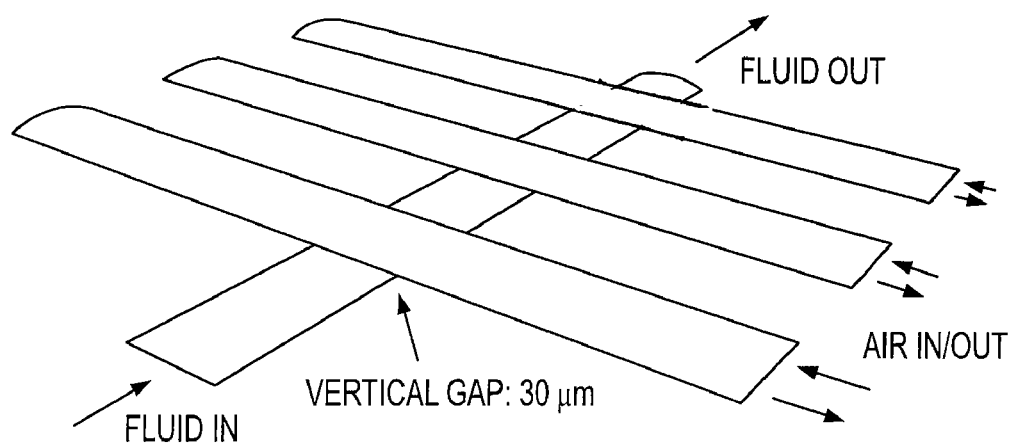
FIG. 4A is a schematic illustration of an elastomeric peristaltic pump located above a fluid flow channel.
Figure 4B:
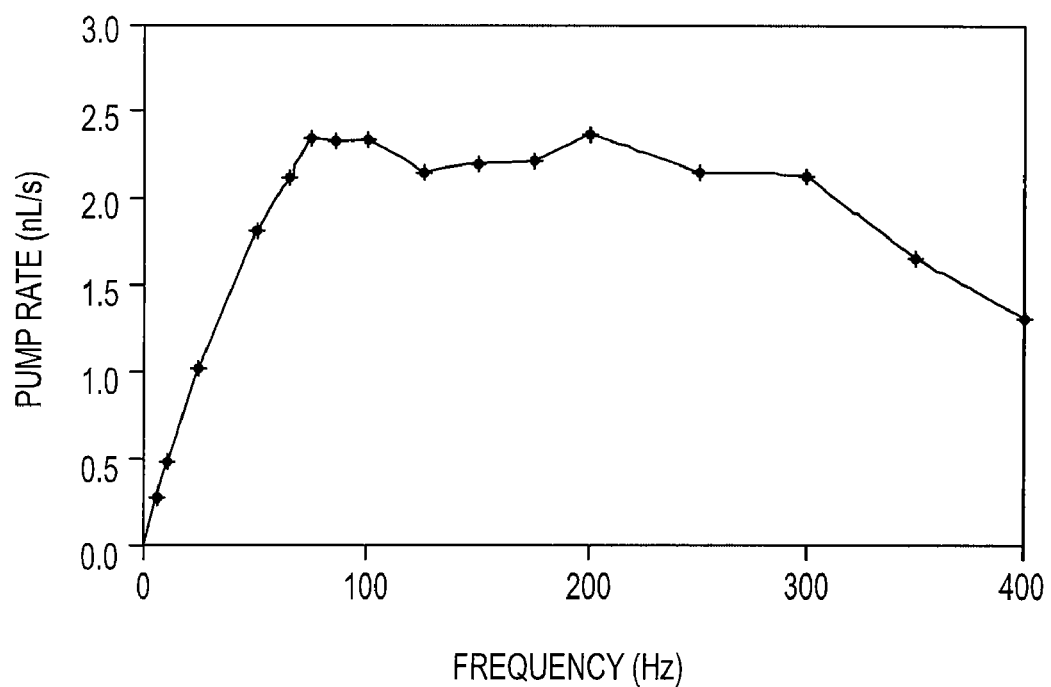
FIG. 4B is a graph showing pump rate (i.e., fluid flow rate) versus frequency of peristaltic pump of FIG. 4A.

It has been found by the present inventors that to achieve this minute fluid sample flow rate, a microfluidic device that is constructed using multi-layer soft lithography having one or more elastomeric pumps 34 is particularly useful. See for example, Unger et al, Science, 2000, 288, 113-116, and U.S. patent application Ser. No. 09/09/605,520, filed Jun. 27, 2000, all of which are incorporated herein by reference in their entirety. Thus, preferred microfluidic devices of the present invention can further comprise a second elastic layer 30 which comprises one or more pump and/or valve systems. These pumps and valves allow control of fluid flow within the fluid flow channel 18 by selectively closing and opening particular sections of fluid flow channel 18. Furthermore, the rate of fluid flow within the fluid flow channels can be controlled by these pumps. These pumps are capable of delivering pico- to nanoliter per minute of fluid flow rates though fluid flow channels within microfluidic devices to the capillary nozzle 14. For example, using the fluid channel arrangement shown in FIG. 4A, where the channels are 100 μm wide and 10 μm high, with 30 μm gap between the fluid channel 18 and the pressure channels 50, the rate of fluid flow through the fluid channel 18 is measured as a function of peristaltic pump 34 (i.e., opening and closing of each pressure channels 50) frequency. Peristalsis is actuated by the pattern 101, 100, 110, 010, 011, 001, where 0 an 1 indicate "valve open" and "valve closed," respectively. FIG. 4B shows the pump rate (nL/s) per peristalsis frequency. By reducing the frequency of the pump 34 and/or the dimensions of the fluid channel 18, one can easily adjust the fluid flow rate within the fluid channel 18 to pico- to nanoliter per minute.

Preferably, microfluidic devices of the present invention are capable of delivering from about 0.5 nL/min to about 200 nL/min of fluid sample to the analytical device, more preferably from about 10 nL/min to about 50 nL/min, and most preferably from about 10 nL/min to about 20 nL/min. These minute delivery rate allows a very minute quantity of analyte in the fluid sample to be injected into the analytical device 120 over a much longer period of time than otherwise possible using conventional means. This constant stream of the fluid sample over a relatively long period of time allows accurate analysis of minute quantities of analytes.

Another advantage of pump-driven elastomeric microfluidic devices of the present invention over current microfluidic devices that use electrokinetic flow means is that electric fields are not required to drive the flow of the solvent, therefore the rate of fluid flow is composition independent. Moreover, electrokinetic flow requires a high salt concentration buffer solution to affect fluid sample flow. The inclusion of high salt concentrations in the buffer creates problems with ionization in ESI and causes a significant background noise. Since microfluidic devices of the present invention do not require electric fields, they eliminate the need for a high salt concentration buffer solution, thereby reducing the background noise and increasing the sensitivity of the analytical device. Furthermore, the lack of requirement for a high salt concentration buffer solution also allows the use of non-aqueous solvents, thereby greatly extending the field of application of these devices.

Figure 5:
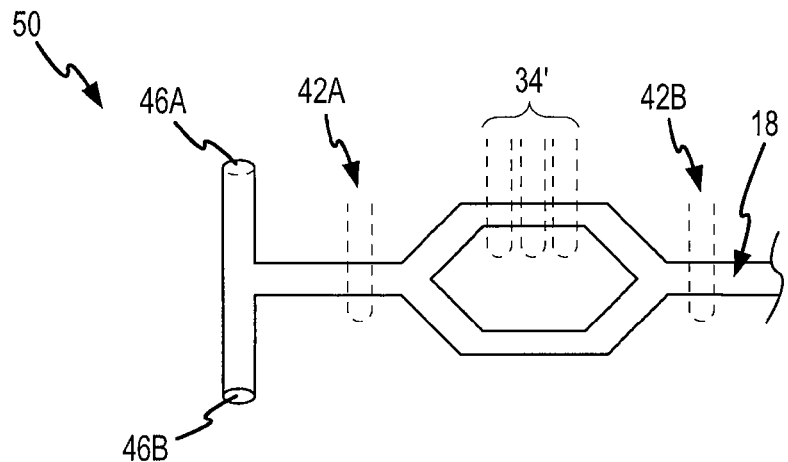
FIG. 5 is a schematic illustration of a fluid flow channel comprising a sample preparation chamber and reagent injection sites.

Microfluidic devices of the present invention can also comprise a sample preparation chamber within the fluid flow channel 18. In this manner, the analyte sample can be prepared and injected into the analytical device 120 directly. The sample preparation chamber can be any configuration which allows preparation of analyte to be analyzed. For example, the sample preparation chamber can be an array of fluid flow channels and pressure channels (i.e., pumps and valves) which can be used in combinatorial synthesis. Exemplary microfluidic devices for combinatorial synthesis are disclosed in Patent Application entitled "Combinatorial Synthesis System," filed on Oct. 3, 2000, by R. Michael van Dam, Marc Unger and Stephen Quake, and further identified as appliation Ser. No. 09/679,432. As shown in FIG. 5, the sample preparation chamber can include or be a rotary fluid flow channel 50 and a means for circulating a fluid (e.g., by using circulation pumps 34' and closing valves 42A and 42B) within the rotary fluid flow channel 50. The rotary fluid channel 50 can be used to conduct a chemical reaction, an assay, protein degradation, separation, or other sample preparations processes.

Figure 2A:
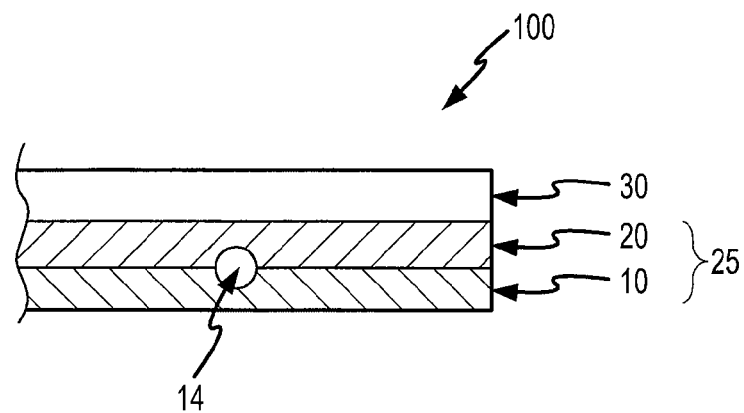
FIG. 2A is a front view of a microfluidic device comprising a fused silica capillary nozzle which can be used as an electrospray source.
Figure 2B:
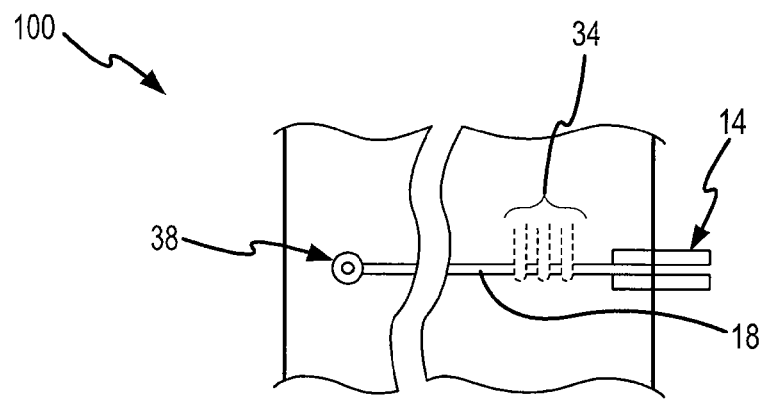
FIG. 2B is a top view illustrating a portion of microfluidic device which comprises pumps (dotted line) on a layer above the fluid flow channel (solid line)
Figure 2C:
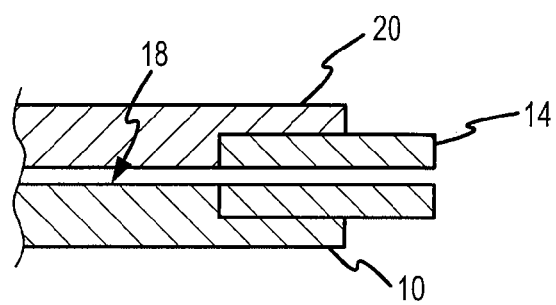
FIG. 2C is a close-up view of one particular embodiment of an interface between a fluid flow channel in microfluidic device and a capillary tube which is used as a means to deliver a fluid sample to an analytical device (not shown)

For example, chemical reaction can be conducted by introducing reagents through fluid flow channels 18 using one or more sample or reagent injection ports 46A and 46B (see FIG. 5). The reagents are then pumped by the pump 34 (e.g., see FIG. 2B) which can be located anywhere along the fluid flow channel 18. These reagents can be admixed and allowed to react for a period of desired time by "holding" the reaction mixture within the rotary fluid flow channel 50 by closing the valves 42A and 42B and optionally circulating the reaction mixture within the rotary fluid channel using the circulation pump 34'. Once the chemical reaction is complete (or after a certain period of time) the valves 42A and 42B are opened and the reaction mixture is pumped through the fluid flow channel 18 by the pump 34 into the capillary nozzle 14, which is connected to a sample injection port 114 of the analytical device 120. The reaction mixture is then injected into the analytical device 120 and the reaction product(s) are analyzed directly.

In an assay sample preparation, desired compounds, enzymes or cells are immobilized on the surface of sample preparation chamber. Methods for immobilizing these materials on a solid support containing functional groups such as hydroxides or amines is well known to one of ordinary skill in the art. For example, U.S. Pat. Nos. 5,424,186 and 5,959,098, which are incorporated herein by reference in their entirety, describe immobilization of polymers such as oligonucleotides and peptides on solid support. If the inner surface of sample preparation chamber is hydrophobic, it can be functionalized with hydrophilic functional groups. For example, a hydrophobic elastomer surface can be treated with oxygen or water plasma to introduce hydroxy functional groups, which can then be used to immobilize desired materials. After desired materials are immobilized, a mixture of compounds is then introduced into the sample preparation chamber. The mixture of compounds can be exposed to the immobilized material for desired time by circulating the mixture within the sample preparation chamber, or alternatively the mixture of compounds can be exposed to the immobilized material by allowing the mixture to simply flow through the sample preparation chamber (in which case the sample preparation chamber need not be a rotary fluid flow channel). The appropriate target compound then bind to the immobilized material while other compounds are washed away. After removing non-binding compounds, the bound compounds can be released from the immobilized material, e.g., by adding more a strongly binding competitive binding compounds or by denaturing the enzyme to release the bound compounds. The released compounds can then be injected into the analytical device directly and analyzed.

The sample preparation chamber can also be used to degrade proteins into smaller components (e.g., oligonucleotides or amino acids) for analysis. For example, one can integrate a tryptic proteolysis of a peptide on the microfluidic device 100 and inject the resulting sample into the analysis device 120 for analysis. For a representative illustration of a tryptic proteolysis of a peptide see Xue et al., *Rapid Commun. Mass Spectrom.*, 1997, 11, 1253, which is incorporated herein by reference in its entirety. In addition, a peptide can be degraded in the sample preparation chamber by immobilizing an enzyme, as described above, which is capable of degrading the peptide and introducing the peptide into the sample preparation chamber. The degraded peptide components can then be effused into a mass spectrometer for analysis. Such peptide sequencing using a mass spectrometer is well known to one of ordinary skill in the art. See for example, Shevchenko et al., *Rapid Commun. Mass Spectrom.*, 1997, 11, 1015-1024, which is incorporated herein by reference in its entirety.

Briefly, Shevchenko et al. describe a rapid peptide sequencing using a combination of nanoelectrospray quadrupole/time-of flight mass spectrometer and isotopic labeling of the peptide. By analyzing the mass spectrum pattern of fragments of peptides and comparing the results with known database of peptide mass spectrum patterns, Shevchenko et al. were able to sequence a peptide relatively quickly.

Alternatively, the sample preparation chamber can be a DNA sorter as disclosed by Chou et al., *Proc. Natl. Acad. Sci.*, 1999, 11-13, or a cell sorter as disclosed in PCT Patent Application Publication No. WO 99/61888, which are incorporated herein by reference in their entirety. Thus, compounds can be sorted based on, e.g., a particular fluorescence wavelength and analyzed by the analytical device.

In addition, by having a portion of the fluid flow channel filled with affinity sieves or similar chromatography material, a mixture of compounds can be separated and each compounds can be analyzed separately.

It should be appreciated that one or more of the above described sample preparation steps can be combined sequentially to provide a variety of sample preparation combinations. For example, sample preparation step can include preparing (i.e., synthesizing) compounds in one sample preparation chamber which is connected to another sample preparation chamber for assaying the compounds, e.g., for enzyme binding. In this manner, a variety of manipulations can be conducted in a single microfluidic device or a combination of microfluidic devices before injecting the analyte into the analytical device for analysis (e.g., identification).

Methods of Fabricating Microfluidic Devices

One exemplary method of fabricating microfluidic devices of the present invention is provided herein, which is similar to methods disclosed in U.S. patent application Ser. No. 09/605, 520, which was previously incorporated by reference. It is to be understood that the present invention is not limited to fabrication by this method. Rather, other suitable methods of fabricating the present microstructures, including modifying the present methods, are also contemplated to be within the scope of the present invention.

Figure 3A:
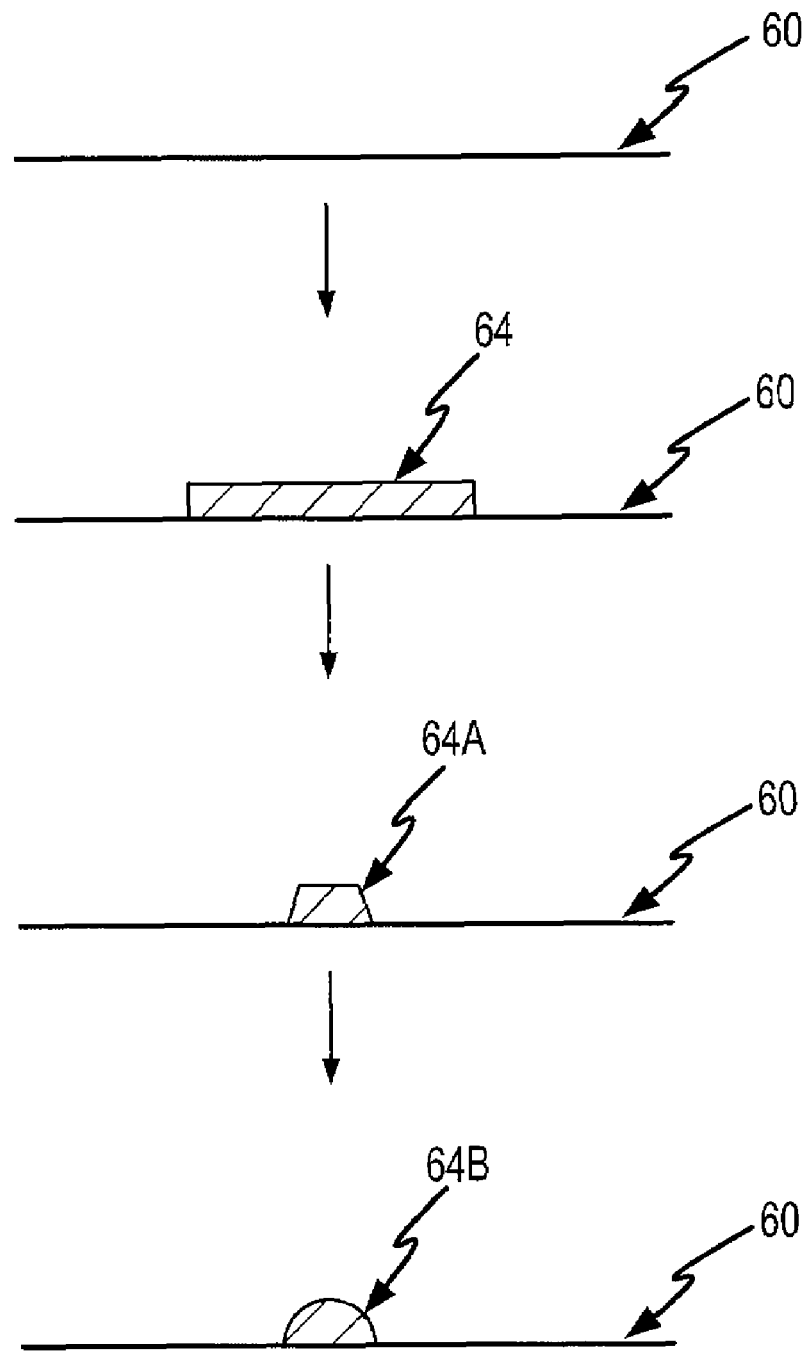
FIGS. 3A and 3B are a schematic illustration of creating an arcuate (e.g., rounded) fluid flow channel elastomer using a photoresist mold.
Figure 3B:
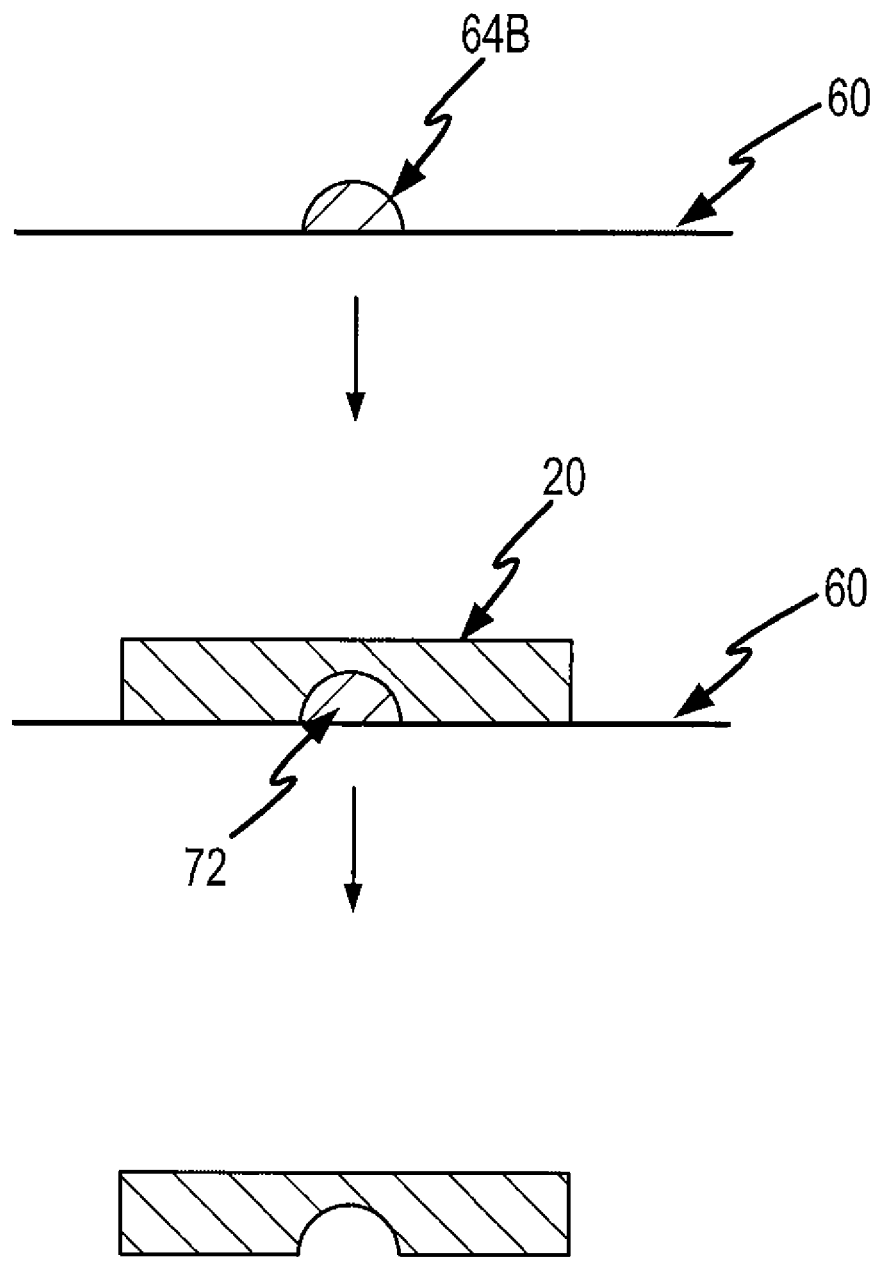

FIGS. 3A and 3B illustrate sequential steps of a preparing a rounded (i.e., circular cross-section) fluid flow channel. Preferably, channels are molded in each layer of the elastomer using soft lithography. A thin layer of photoresist 64 is spin coated on to a wafer 60. The photoresist is exposed using a high transparency film as a mask (not shown) with desired pattern. The exposed photoresist is then developed to provide a mold (for clarity only one flow channel mold 64A is shown). The height of flow channel mold 64A depends on the thickness of the photoresist. If desired, multiple layers of photoresist can be applied to achieve the desired thickness, using intermediate 'hard bake,' which generally involves heating (e.g., to about 120° C.) to fix channel structures in one part of the device prior to creation of the bottom portion 10 or a second layer 30. This approach can be used to create regions with different channel depth in different parts of the same device.

Typically, the exposure and development of a photoresist results in a trapezoidal shaped mold. The photoresist is then heated (e.g., at 200° C. for about 30 minutes) to "reflow" the photoresist, thereby producing a rounded flow channel mold 64B. This "rounding" facilitates sealing of capillaries of different dimensions within the device. A layer of elastomer 20 (i.e., top portion of the first elastic layer) is then spin coated on to the mold, as shown in FIG. 3B. After curing, the elastomer is removed from the mold to provide a recess which becomes a part of the flow channel 18. A complimentary bottom portion elastomer 10 is produced and combined with the top portion 20 to produce a first elastomer layer 25. A second elastic layer 30 comprising pump 34 and valve 42 systems is then produced as a single layer and bonded together with (i.e., affixed on top of) the first elastic layer 25.

Figure 6A:
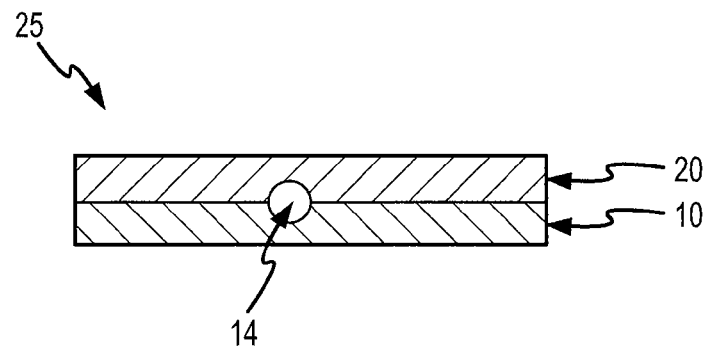
FIG. 6A is a front view of the first elastic layer integrated with a capillary nozzle.
Figure 6B:
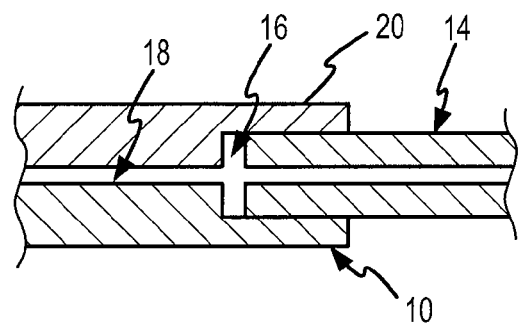
FIG. 6B is a side cross-sectional view of the first elastic layer fitted with a capillary nozzle with dead volume in between the fluid channel and the capillary nozzle.

Upon casting in elastomer, such as GE Silicones RTV615 or Dow Corning Sylgard, a channel is created whose depth is dependent on the thickness of the photoresist upon the wafer. The capillary nozzle 14 is formed by placing a capillary nozzle (e.g., a drawn silica capillary) in the flow channel 18, so that the capillary nozzle 14 sits within the flow channel 18 and extends beyond the edge of the microfluidic device 100. Typically, the distance of the capillary nozzle extension beyond the edge of the microfluidic device 100 is from about 50 µm to about 5 mm, preferably from about 100 µm to about 2 mm, and more preferably from about 100 µm to about 1 mm. However, the distance of the extension can be longer depending on a particular application. The capillary 14 is sealed within two portions (FIGS. 6A and 6B). It can be sealed either directly by baking together the two portions of partially cured elastomers or by incorporation of uncured elastomer (e.g., RTV) during the final bake (i.e., curing) stage.

Fluids are designed to flow in the middle of the two portions (i.e., top portion 20 and bottom portion 10) of this device. The alignment of the capillary 14 between the two portions and its juxtaposition with the fluid channel 18 can create a partial occlusion of the capillary if the capillary is perfectly centered between the layers.

Better alignments can be achieved by creating an offset in the depths (i.e., height) of two portions of the channels between which the capillary is fitted. For example, if the depth of the photoresist for the lower portion is 5 microns less than the upper portion of the first elastic layer 25, a capillary with a ten-micron internal diameter can be accommodated without a significant offset.

Figure 6C:
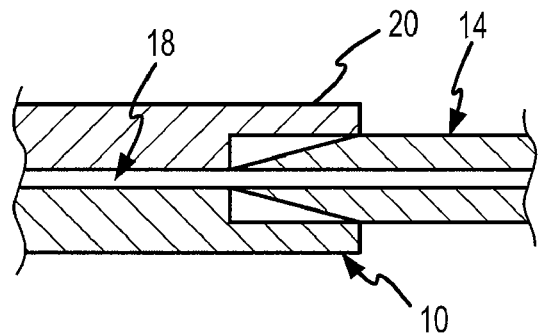
FIG. 6C is a side cross-sectional view of the first elastic layer fitted with a capillary nozzle having a tapered fitting end which reduces the amount of dead volume.

The portion of fluid flow channel 18 which becomes integrated with the capillary nozzle 14 is configured such that the fluid sample flows directly from the microfluidic device 100 to the analytical device (e.g., mass spectrometer). Additional features patterned in photoresist may be necessary to reduce potential dead volume 16 at the junction between the capillary 14 and the fluid flow channel 18. Alternative, the amount of dead volume can be reduced by using a tapered capillary as shown in FIG. 6C.

This configuration is compatible with commercially available drawn silica capillaries and custom-drawn capillaries. The dimensions of the capillaries that can be accommodated in this configuration include, but are not limited to, capillaries with internal diameters of from about 1 µm to about 100 µm and outer diameters of from about 20 µm to about 360 µm.

In order to create 'pump' and 'valve' features within the microfluidic device 100, a second elastic layer 30 having 'control line' features (for pumps and valves) is bonded on top of the first elastic layer. This second elastic layer is prepared using a similar process for the above described top or bottom portions of the first elastic layer. Typically, the second elastic layer is then baked (or cured) together with the first elastic layer to create the final device.

Figure 7A:
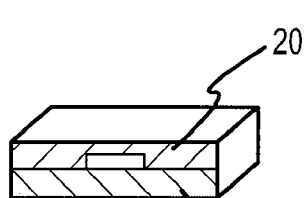
FIG. 7A is a perspective view of the first elastic layer having a rectangular cross-section fluid flow channel.
Figure 7B:
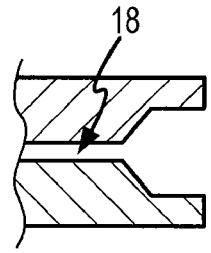
FIG. 7B is a cut-away view along 1-1' of FIG. 7A showing a tapered portion of fluid flow channel which is designed to reduce the amount of dead volume between the capillary nozzle and the fluid flow channel.
Figure 7C:
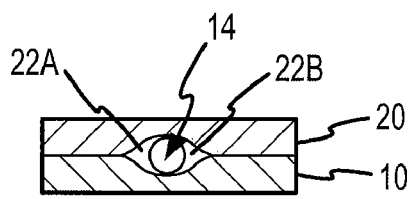
FIG. 7C is a front view of the first elastic layer fitted with a capillary nozzle illustrating a possible gap formation between the capillary nozzle and the fluid flow channel.
Figure 8:
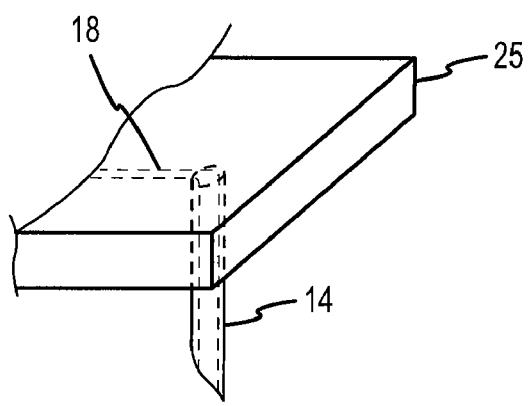
FIG. 8 is another embodiment of attaching a capillary nozzle to a microfluidic device of the present invention through the Z-axis.

The capillary 14 can be sealed within the microfluidic device 100, by a variety of processes. For example, the capillary 14 can be sealed during baking together of the two portions of the first elastic layer 25. Alternatively, as shown in FIGS. 7A-7C, the capillary is 'push-fit' into the device between two portion of the first elastic layer 25, thereby creating an instant seal. The dimensions of the push-fit envelope are chosen to accommodate the diameter of the capillary 14. For example, an envelope of about 200 µm width and about 15 µm in height has a perimeter of 430 microns. A capillary with 100 µm outer diameter has a circumference of 314 µm. The seal can be further secured by incorporation of uncured elastomer (e.g., RTV) in the envelope between the two portions (e.g., areas 22A and 22B). As shown in FIG. 8, push fitting can also be used to incorporate a capillary that fits into the device in the 'Z' plane. One major advantage of push fitting is that capillaries can be easily interchanged if clogging occurs.

Application of High Voltage for Electrospray

A high voltage applied to capillary nozzle causes ionization of molecules passing through it at atmospheric pressure and formation of a plasma stream that is accelerated into the analytical device (e.g., mass spectrometer). The system allows for both the sample preparation and sample delivery processes for the ESI-MS to be integrated on the microfluidic device.

Figure 9A:
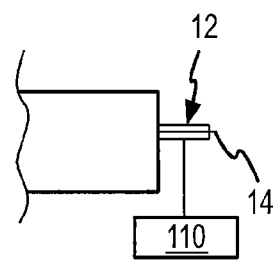
FIG. 9A is a schematic illustration of one embodiment of using a capillary nozzle as an electrospray.
Figure 9B:
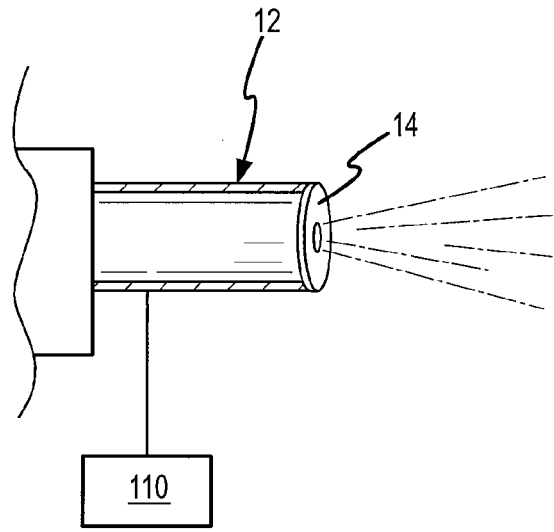
FIG. 9B is a close-up view of the capillary nozzle of FIG. 9A.
Figure 9C:
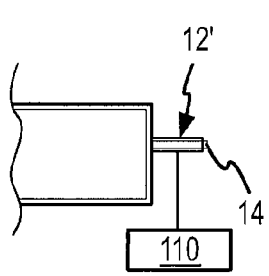
FIG. 9C is a schematic illustration of another embodiment of using a capillary nozzle as an electrospray.
Figure 9D:
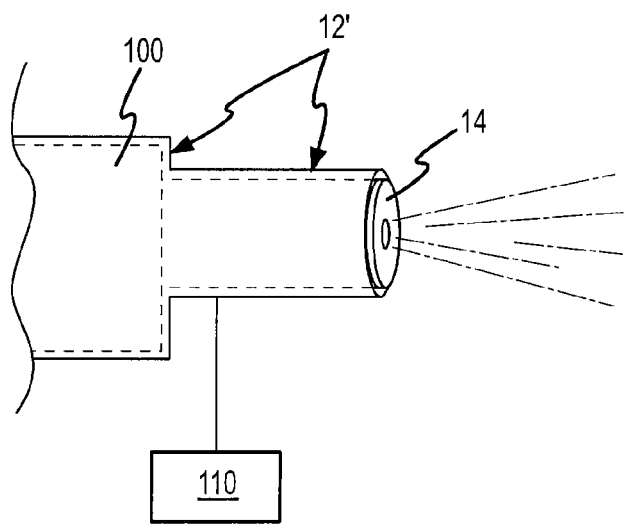
FIG. 9D is a close-up view of the capillary nozzle of FIG. 9C.

Typically application of voltages of from about 500 to about 5 kilovolts (kV) are required to create the electrospray. Two illustrative examples are shown in FIGS. 9A-9D. One method, as shown in FIGS. 9A and 9B uses a metallized (e.g., Pd or Gold) or metal coated capillary, which are commercially available. In this method, a high voltage device 110 applies voltage to capillary 14 having a metal coating 12 which creates electrospray 8. Unfortunately, these types of capillaries have a limited life-span due to evaporation of the metallized layer that carries the charge. Another method uses an external metal sheath capillary as shown in FIGS. 9C and 9D. In this embodiment, a high voltage device 110 applies voltage to capillary 14 having a metal sheath 12' to create electrospray 8. This method has the added benefit that it can be built into a plastic housing for the device and the capillary itself can be used for more than one sample.

Applications

The integrated microfluidic devices that consist of fluid flow channels, pumps and valves can be used in a variety of applications as discussed above. In addition, such devices can be used as nanoliter-scale fluid delivery devices for reliably delivering highly homogeneous, nanoliter volumes (e.g., from about 1 nL/min to about 200 nL/min) of fluid to the mass spectrometer interface. Such devices can also be used as nanoliter-scale devices which integrate sample purification, separation and processing, as discussed in detail above. This reduces sample preparation cost, avoids sample cross contamination, and enables the application of mass spectrometry to other areas of interest, such as medical diagnostics. Furthermore, such devices can be interfaced with a robotic auto sampler to provide high throughput nanospray device. In one example of this device, multiple channels are created in the elastomer, each of which is operated by a single set of pumps and individually sampled using a control valve.

Microfluidic devices of the present invention are useful in proteomics such as classic proteomics, e.g., identification and quantitation of unknown proteins identified using 1-D and 2-D gel electrophoresis, and functional proteomics, e.g., analysis of molecular interactions. In addition, microfluidic devices of the present invention are also useful in drug or target molecule discovery. NanoES MS/MS is the most powerful approach currently available, as it allows unambiguous protein and peptide fragment data to be queried against EST and genomic databases. For example, a protein identified as differentially expressed or with variable post-translational modification when two samples or tissues are compared can be identified by comparing the peptide sequences obtained by mass spectrometry against EST and genomic databases.

Moreover, the identified nucleotide sequences, combined with the peptide sequences generated by mass spectrometry, can be used for cloning the protein, in downstream assay development, target validation. And as discussed in detail above, on-chip digestion (i.e., degradation) of proteins with proteases (for example using immobilized trypsin) and on-chip separations can also be achieved by using microfluidic devices of the present invention.

In addition, microfluidic devices of the present invention can be used to assist in drug development by enabling unambiguous identification of metabolites in serum, urine, etc. Furthermore, microfluidic devices of the present invention can be used in ADME/PK (absorption-distribution-metabolism-excretion/pharmacokinetic) studies. Additionally, high throughput screening can be conducted directly by using the MS to provide assay readout.

Other uses for microfluidic devices of the present invention include, but are not limited to, applications in genomics, e.g. high throughput genotyping, applications in analytical chemistry, on chip separations, on-chip combinatorial chemistry, and analysis of proteins in clinical diagnostics.

In particular, the sample preparation chamber can be used for conducting a chemical reaction; conducting an assay; degrading a peptide or protein; conducting a chemical analysis; extraction of analytes from solvents (aqueous/non-aqueous); extraction of analytes from bodily fluids; concentration of sample analytes; affinity purification of an analyte; digesting a nucleic acid, carbohydrate, lipid or other molecule or mixture of molecules; separation; and cell growth (mammalian, bacterial or parasite).

In combinatorial synthesis, microfluidic devices of the present invention can us a monomer (i.e., starting material) that is selected from the group consisting of nucleotides, amino acid peptides, carbohydrates, lipids, and other precursors for combinatorial synthesis.

The sample preparation step can also comprise binding a target molecule to an array of oligonucleotides, peptides, proteins, oligosaccharides, and small molecules (e.g., drugs).

Preferred Layer and Channel Dimensions

Microfabricated refers to the size of features of an elastomeric structure fabricated in accordance with an embodiment of the present invention. In general, variation in at least one dimension of microfabricated structures is controlled to the micron level, with at least one dimension being microscopic (i.e. below 1000 μm). Microfabrication typically involves semiconductor or MEMS fabrication techniques such as photolithography and spin coating that are designed for to produce feature dimensions on the microscopic level, with at least some of the dimension of the microfabricated structure requiring a microscope to reasonably resolve/image the structure.

For integration with an electrospray capillary for use in a mass spectrometer, preferred width-to-depth ratios of a rectangular cross-section fluid flow channel 18 is from about 0.1:1 to about 100:1, more preferably from about 1:1 to about 50:1, still more preferably from about 2:1 to about 20:1, and most preferably from about 3:1 to about 15:1. For a circular cross-section fluid flow channel 18, preferred diameter is from about 1 μm to about 500 μm, more preferably from about 1 μm to about 200 μm, and most preferably from about 3 μm to about 200 μm.

The flow channels are not limited to these specific dimension ranges and examples given above, and can vary depending on a particular sample delivery means employed. For example, wider flow channels having a diameter in the order of about 1000 μm may be useful in other analytical device interface, such as HPLC or UV spectrometer.

The thickness of the first elastomeric layer 25 also depends on a particular application. For use in electrospray-MS with nL/min sample deliver rate, the first elastomeric layer 25 has thickness of from about 40 μm to about 10 mm, preferably from about 40 μm to about 5 mm, and more preferably from about 40 μm to about 3 mm.

Accordingly, the layer of elastomer separating the flow channel 18 and the pressure channel (e.g., pumps and valves) has a typical thickness of from about 0.01 μm to about 1000 μm, preferably from about 0.05 μm to about 500 μm, more preferably from about 0.2 μm to about 250 μm, still more preferably from about 1 μm to about 100 μm, yet still more preferably from about 2 μm to about 50 μm, and most preferably from about 5 μm to about 40 μm.

The pressure channels that make up the pump and valve systems typically have rectangular cross-section for ease of fabrication. However, the cross-section is not limited to such shape. Preferably the width of pressure channels is from about 0.01 μm to about 1000 μm, preferably from about 0.05 μm to about 1000 μm, more preferably from about 0.2 μm to about 500 μm, still more preferably from about 1 μm to about 250 μm, and most preferably from about 10 μm to about 200 μm. The thickness of the second elastomeric layer 30 is from about 50 μm to several centimeters, preferably from about 0.1 μm to about 10 cm, more preferably from about 1 μm to about 5 cm, still more preferably from about 10 μm to about 2 cm, and most preferably from about 100 μm to about 10 mm.

Multilayer Soft Lithography Construction Techniques and Materials

Preferably, elastomeric portions 10 and 20 (and elastomeric layer 25 and 30) are bonded together chemically, using chemistry that is intrinsic to the polymers comprising the patterned elastomer layers. Most preferably, the bonding comprises two component "addition cure" bonding.

In a preferred aspect, the layers (or portions) of elastomer are bound together in a heterogenous bonding in which the layers have a different chemistry. Alternatively, a homogenous bonding can be used in which all layers would be of the same chemistry. Thirdly, the respective elastomer layers can optionally be glued together by an adhesive instead. In a fourth aspect, the elastomeric layers can be thermoset elastomers bonded together by heating.

In one aspect of homogeneous bonding, the elastomeric layers are composed of the same elastomer material, with the same chemical entity in one layer reacting with the same chemical entity in the other layer to bond the layers together. In one embodiment, bonding between polymer chains of like elastomer layers can result from activation of a crosslinking agent due to light, heat, or chemical reaction with a separate chemical species.

Alternatively in a heterogeneous aspect, the elastomeric layers are composed of different elastomeric materials, with a first chemical entity in one layer reacting with a second chemical entity in another layer. In one exemplary heterogenous aspect, the bonding process used to bind respective elastomeric layers together can comprise bonding together two layers of RTV 615 silicone. RTV 615 silicone is a two-part addition-cure silicone rubber. Part A contains vinyl groups and catalyst; part B contains silicon hydride (Si—H) groups. The conventional ratio for RTV 615 is 10A:1B. For bonding, one layer can be made with 30A:1B (i.e. excess vinyl groups) and the other with 3A:1B (i.e. excess Si—H groups). Each layer is cured separately. When the two layers are brought into contact and heated at elevated temperature, they bond irreversibly forming a monolithic elastomeric substrate.

In an exemplary aspect of the present invention, elastomeric structures are formed utilizing Sylgard 182, 184 or 186, or aliphatic urethane diacrylates such as (but not limited to) Ebecryl 270 or Irr 245 from UCB Chemical.

Alternatively, other bonding methods can be used, including activating the elastomer surface, for example by plasma exposure, so that the elastomer layers/substrate bond when placed in contact. For example, one approach to bonding together elastomer layers composed of the same material is set forth by Duffy et al, "Rapid Prototyping of Microfluidic Systems in Poly(dimethylsiloxane)", *Analytical Chemistry*, 1998, 70, 4974-4984, which is incorporated herein by reference in its entirety. This paper discusses that exposing polydimethylsiloxane (PDMS) layers to oxygen plasma causes oxidation of the surface, with irreversible bonding occurring when the two oxidized layers are placed into contact.

Yet another approach to bonding together successive layers of elastomer is to utilize the adhesive properties of uncured elastomer. Specifically, a thin layer of uncured elastomer such as RTV 615 is applied on top of a first cured elastomeric layer. Next, a second cured elastomeric layer is placed on top of the uncured elastomeric layer. The thin middle layer of uncured elastomer is then cured to produce a monolithic elastomeric structure. Alternatively, uncured elastomer can be applied to the bottom of a first cured elastomer layer, with the first cured elastomer layer placed on top of a second cured elastomer layer. Curing the middle thin elastomer layer again results in formation of a monolithic elastomeric structure.

Suitable Elastomeric Materials

Allcock et al, *Contemporary Polymer Chemistry*, $2^{nd}$ Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Elastomeric materials having a Young's modulus of between about 1 Pa-1 TPa, more preferably between about 10 Pa-100 GPa, still more preferably between about 20 Pa -1 GPa, yet more preferably between about 50 Pa-10 MPa, and most preferably between about 100 Pa-1 MPa are useful in accordance with the present invention. It should be appreciated, however, elastomeric materials having a Young's modulus outside of these ranges can also be utilized depending upon the needs of a particular application.

Microfluidic devices of the present invention can be fabricated from a wide variety of elastomers. In an exemplary aspect, elastomeric layers 25 and 35 are preferably fabricated from silicone rubber. However, other suitable elastomers may also be used.

In an exemplary aspect of the present invention, microfluidic devices are fabricated from an elastomeric polymer such as GE RTV 615 (formulation), a vinyl-silane crosslinked (type) silicone elastomer (family). However, microfluidic devices of the present invention are not limited to this one formulation, type or even this family of polymer; rather, nearly any elastomeric polymer is suitable. In the case of multilayer soft lithography, preferably layers of elastomer are cured separately and then bonded together. This scheme requires that cured layers possess sufficient reactivity to bond together. Either the layers can be of the same type, and are capable of bonding to themselves, or they can be of two different types, and are capable of bonding to each other. Other possibilities include the use an adhesive between layers and the use of thermoset elastomers.

Given the tremendous diversity of polymer chemistries, precursors, synthetic methods, reaction conditions, and potential additives, there are a huge number of possible elastomer systems that could be used to make microfluidic devices of the present invention. Variations in the materials used depends on the need for particular material properties, i.e. solvent resistance, stiffness, gas permeability, or temperature stability.

There are a variety of types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones.

Polyisoprene, polybutadiene, polychloroprene

Polyisoprene, polybutadiene, and polychloroprene are all polymerized from diene monomers, and therefore have one double bond per monomer when polymerized. This double bond allows the polymers to be converted to elastomers by vulcanization (essentially, sulfur is used to form crosslinks between the double bonds by heating). This would easily allow homogeneous multilayer soft lithography by incomplete vulcanization of the layers to be bonded; photoresist encapsulation would be possible by a similar mechanism.

Polyisobutylene

Pure polyisobutylene has no double bonds, but is crosslinked to use as an elastomer by including a small amount (~1%) of isoprene in the polymerization. The isoprene monomers give pendant double bonds on the polyisobutylene backbone, which may then be vulcanized as above.

Poly(styrene-butadiene-styrene)

Poly(styrene-butadiene-styrene) is produced by living anionic polymerization (that is, there is no natural chain-terminating step in the reaction), so "live" polymer ends can exist in the cured polymer. This makes it a natural candidate for the present photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes

Polyurethanes are produced from di-isocyanates (A-A) and di-alcohols or di-amines (B-B); since there are a large variety of di-isocyanates and di-alcohols/amines, the number of different types of polyurethanes is huge. The A vs. B nature of the polymers, however, would make them useful for heterogeneous multilayer soft lithography just as RTV 615 is: by using excess A-A in one layer and excess B-B in the other layer.

Silicones

Silicone polymers probably have the greatest structural variety, and almost certainly have the greatest number of commercially available formulations. The vinyl-to-(Si—H) crosslinking of RTV 615 (which allows both heterogeneous multilayer soft lithography and photoresist encapsulation) has already been discussed, but this is only one of several crosslinking methods used in silicone polymer chemistry.

Cross Linking Agents

In addition to the use of the simple "pure" polymers discussed above, crosslinking agents can also be added. Some agents (like the monomers bearing pendant double bonds for vulcanization) are suitable for allowing homogeneous (A to A) multilayer soft lithography or photoresist encapsulation; in such an approach the same agent is incorporated into both elastomer layers. Complementary agents (i.e. one monomer bearing a pendant double bond, and another bearing a pendant Si—H group) are suitable for heterogeneous (A to B) multilayer soft lithography. In this approach complementary agents are added to adjacent layers.

Other Materials

In addition, polymers incorporating materials such as chlorosilanes or methyl-, ethyl-, and phenylsilanes, and polydimethylsiloxane (PDMS) such as Dow Chemical Corp. Sylgard 182, 184 or 186, or aliphatic urethane diacrylates such as (but not limited to) Ebecryl 270 or Irr 245 from UCB Chemical can also be used.

The following is a non-exclusive list of elastomeric materials which can be utilized in connection with the present invention: polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), poly(carborane-siloxanes) (Dexsil), poly(acrylonitrile-butadiene) (nitrile rubber), poly (1-butene), poly(chlorotrifluoroethylene-vinylidene fluoride) copolymers (Kel-F), poly(ethyl vinyl ether), poly(vinylidene fluoride), poly(vinylidene fluoride—hexafluoropropylene) copolymer (Viton), elastomeric compositions of polyvinylchloride (PVC), polysulfone, polycarbonate, polymethylmethacrylate (PMMA), and polytertrafluoroethylene (Teflon).

Doping and Dilution

Elastomers can also be "doped" with uncrosslinkable polymer chains of the same class. For instance RTV 615 may be diluted with GE SF96-50 Silicone Fluid. This serves to reduce the viscosity of the uncured elastomer and reduces the Young's modulus of the cured elastomer. Essentially, the crosslink-capable polymer chains are spread further apart by the addition of "inert" polymer chains, so this is called "dilution". RTV 615 cures at up to 90% dilution, with a dramatic reduction in Young's modulus.

Pre-Treatment and Surface Coating

Once the elastomeric material has been molded or etched into the appropriate shape, it can be pre-treated in order to facilitate operation in connection with a particular application. For example, in sorting biological entities such as cells or DNA the hydrophobic nature of the biological entity can cause it to adhere to the hydrophobic elastomer of the walls of the channel. Therefore, it is useful to pre-treat the elastomeric structure order to impart a hydrophilic character to the channel walls. In an embodiment of the present invention utilizing the General Electric RTV 615 elastomer, this can be accomplished by boiling the shaped elastomer in acid (e.g. 0.01% HCl in water, pH 2.7, at 60° C. for 40 min).

Other types of pre-treatment of elastomer material are also contemplated by the present application. For example, certain portions of elastomer can be pre-treated to create anchors (i.e., immobilization site) for surface chemistry reactions (for example in the formation of peptide chains), or binding sites for antibodies.

Methods of Operating Microfluidic Devices of the Present Invention

Methods for pumping fluids and opening or closing valve systems are disclosed in the above mentioned U.S. patent application Ser. No. 09/605,520, which was previously incorporated by reference in its entirety.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All publications, patents, and patent applications cited herein are hereby incorporated by reference in their entirety.

What is claimed is:

1. A method for providing a nanoliter volume of a fluid sample from a microfluidic device into an analytical device, the method comprising the steps of:
  providing the analytical device;
  providing the microfluidic device, wherein the microfluidic device comprises:
    a first elastomeric layer having a fluid flow channel disposed therein,
    a second elastomeric layer positioned in contact with the first elastomeric layer, wherein the second elastomeric layer has an integrated microfluidic pump disposed therein, and wherein the pump controls the flow of fluid through the fluid flow channel,
    a sample preparation chamber coupled to the fluid flow channel, the sample preparation chamber comprising a rotary fluid flow channel, and
    a capillary having at least a portion fitted within the fluid flow channel, wherein the capillary comprises a nozzle, and wherein the capillary is interconnected to the analytical device for introducing the fluid sample from the fluid flow channel to the analytical device; and
  injecting at least a portion of the fluid sample from the microfluidic device directly into the analytical device through the capillary nozzle.

2. The method of claim 1, wherein the microfluidic pump is a peristaltic pump.

3. The method of claim 1, wherein the fluid sample comprises a non-aqueous solvent.

4. The method of claim 1, wherein the capillary nozzle is an electrospray nozzle.

5. The method of claim 4, wherein the fluid sample injected into the analytical device through the capillary nozzle is converted into a mist while exiting the nozzle.

6. The method of claim 5, wherein the capillary nozzle is coupled to a device for applying a voltage to the capillary.

7. The method of claim 4, wherein the analytical device is an electrospray mass spectrometer.

8. The method of claim 1, wherein the analytical device is selected from the group consisting of UV spectrometers, fluorescence spectrometers, IR spectrometers, gas chromatographic devices, liquid chromatographic devices, NMR devices, mass spectrometers and combinations thereof.

9. The method of claim 1, wherein an electric field is not used to control the flow of fluid through the fluid flow channel of the microfluidic device.

10. The method of claim 1, wherein the fluid sample does not contain an ionic buffer to drive electroosmotic flow of the sample through the fluid flow channel.

11. A method for providing a nanoliter volume of a fluid sample from a microfluidic device into an analytical device, the method comprising the steps of:

providing the analytical device;

providing the microfluidic device, wherein the microfluidic device comprises:

a first elastomeric layer having a fluid flow channel disposed therein, a second elastomeric layer having a pressure channel disposed therein, wherein the pressure channel controls the flow of fluid through said fluid flow channel, a sample preparation chamber coupled to the fluid flow channel, the sample preparation chamber comprising a rotary fluid flow channel, and a capillary having at least a portion fitted within the fluid flow channel, wherein the capillary comprises a nozzle, and wherein the capillary is interconnected to the analytical device for introducing the fluid sample from the fluid flow channel to the analytical device; and injecting at least a portion of the fluid sample from the microfluidic device to the analytical device through the capillary nozzle.

12. The method of claim 11, wherein the fluid sample comprises a non-aqueous solvent.

13. The method of claim 11, wherein the capillary nozzle is an electrospray nozzle.

14. The method of claim 11, wherein an electric field is not used to control the flow of fluid through the fluid flow channel of the microfluidic device.

15. The method of claim 11, wherein the fluid sample does not contain an ionic buffer to drive electroosmotic flow of the sample through the fluid flow channel.

16. A system to provide a nanoliter volume of a non-aqueous fluid sample from a microfluidic device to an analytical device, the system comprising:

an analytical device for analyzing at least a portion of the non-aqueous fluid sample; and a microfluidic device for providing the at least portion of the fluid sample to the analytical device, wherein the microfluidic device comprises:

a first elastomeric layer having a fluid flow channel disposed therein, a second elastomeric layer positioned in contact with the first elastomeric layer, wherein the second elastomeric layer has an integrated microfluidic pump disposed therein, and wherein the pump controls the flow of fluid through the fluid flow channel, a sample preparation chamber coupled to the fluid flow channel, the sample preparation chamber comprising a rotary fluid flow channel, and a capillary having at least a portion fitted within the fluid flow channel, wherein the capillary comprises a nozzle, and wherein the capillary is interconnected to the analytical device for introducing the fluid sample from the fluid flow channel to the analytical device.

17. The system of claim 16, wherein the system further comprises a device for applying a voltage to the capillary to aerosolize the fluid sample exiting the capillary nozzle.

18. The system of claim 16, wherein the sample preparation chamber comprises a means for circulating a fluid within said rotary fluid flow channel for conducting a chemical reaction, an assay, or other sample preparations within said rotary fluid flow channel.

19. The system of claim 16, wherein the sample preparation chamber supplies an analyte to the non-aqueous fluid sample that is analyzed by the analytical device.

20. The system of claim 16, wherein the analytical device is a mass spectrometer.

21. The system of claim 20, wherein the mass spectrometer is an electrospray mass spectrometer.

22. A system to provide a nanoliter volume of a non-aqueous fluid sample from a microfluidic device to an analytical device, the system comprising:

an analytical device for analyzing at least a portion of the non-aqueous fluid sample; and a microfluidic device for providing the at least portion of the fluid sample to the analytical device, wherein the microfluidic device comprises:

a first elastomeric layer having a fluid flow channel disposed therein, a second elastomeric layer positioned in contact with the first elastomeric layer, wherein the second elastomeric layer has an integrated microfluidic pump disposed therein, and wherein the pump controls the flow of fluid through the fluid flow channel, and a capillary having at least a portion fitted within the fluid flow channel, wherein the capillary comprises a nozzle, and wherein the capillary is interconnected to the analytical device for introducing the fluid sample from the fluid flow channel to the analytical device; and a sample preparation chamber in fluid communication with the fluid flow channel of the microfluidic device, wherein the sample preparation chamber supplies an analyte to the non-aqueous fluid sample that is analyzed by the analytical device, and wherein the sample preparation chamber comprises a rotary fluid flow channel.

23. The system of claim 22, wherein the sample preparation chamber comprises a pump for circulating fluid within said rotary fluid flow channel for conducting a chemical reaction, an assay, or other sample preparations within said rotary fluid flow channel.

24. The system of claim 23, wherein the means for circulating fluid comprises a pump and valve system for circulating the sample fluid within said rotary chamber.

25. The system of claim 23, wherein the means for circulating the fluid does not include applying an electric field to the fluid circulating in the rotary fluid flow channel.

* * * * *